United States Patent
Wagner et al.

(10) Patent No.: US 7,821,641 B2
(45) Date of Patent: Oct. 26, 2010

(54) PRECISE FLOW-ORIENTED MULTI-ANGLE REMISSION SENSOR

(75) Inventors: Beate Wagner, Neuleiningen (DE); Jürgen Ettmüller, Haβloch (DE); Michael Schäfer, Altrip (DE); Jürgen Lohmann, Münster (DE); Jan Berg, Münster (DE); Andreas Daiss, Mannheim (DE)

(73) Assignee: BASF Corporation, Munster (DE)

( * ) Notice: Subject to any disclaimer, the term of this patent is extended or adjusted under 35 U.S.C. 154(b) by 805 days.

(21) Appl. No.: 10/596,388

(22) PCT Filed: Dec. 22, 2004

(86) PCT No.: PCT/EP2004/014603

§ 371 (c)(1),
(2), (4) Date: Jun. 12, 2006

(87) PCT Pub. No.: WO2005/062022

PCT Pub. Date: Jul. 7, 2005

(65) Prior Publication Data

US 2008/0019887 A1      Jan. 24, 2008

(30) Foreign Application Priority Data

Dec. 22, 2003 (DE) .................. 103 61 058

(51) Int. Cl.
*G01N 1/10* (2006.01)
(52) U.S. Cl. ................... 356/446; 356/246
(58) Field of Classification Search .......... 356/246, 356/446
See application file for complete search history.

(56) References Cited

U.S. PATENT DOCUMENTS

| | | | | |
|---|---|---|---|---|
| 5,412,466 A | * | 5/1995 | Ogino | 356/246 |
| 5,690,895 A | * | 11/1997 | Matsumoto et al. | 356/246 |
| 5,883,721 A | | 3/1999 | Gilby et al. | |
| 2002/0131043 A1 | * | 9/2002 | Steenhoek et al. | 356/328 |
| 2002/0149773 A1 | * | 10/2002 | Martino et al. | 356/436 |
| 2003/0151746 A1 | | 8/2003 | Sperlimg et al. | |

FOREIGN PATENT DOCUMENTS

| | | |
|---|---|---|
| CA | 2531166 A1 | 1/2005 |
| DE | 2445148 A1 | 1/1974 |
| DE | 10149780 A1 | 4/2003 |
| DE | 10330641 A1 | 2/2005 |
| EP | 0472899 A1 | 7/2003 |
| GB | 1471976 | 4/1977 |
| WO | 98/16822 A1 | 4/1998 |

(Continued)

OTHER PUBLICATIONS

"International Preliminary Report on Patentatbility", translation, Jun. 12, 2006, pp. 1-6.*

(Continued)

*Primary Examiner*—Kara E Geisel

(57) ABSTRACT

A three-dimensional flow cell for aligning non-isometric particles in a liquid sample in two axes, a method of aligning non-isometric particles in a liquid sample, the use of the three-dimensional flow cell, a reflectance sensor which has the three-dimensional flow cell according to the invention, a method of measuring the reflectance of a liquid sample containing non-isometric particles and the use of the reflectance sensor according to the invention.

22 Claims, 16 Drawing Sheets

FOREIGN PATENT DOCUMENTS

WO 02/075285 A2 9/2002

OTHER PUBLICATIONS

Kachel V et al.: "Uniform Lateral Orientation, Caused by Flow Forces, of Flat Particles in Flow-Through System" Journal of Histochemistry and Cutochemistry, Histochemistry Society, New York,m NY, US, vol. 25, No. 7, 1977, pp. 774-780; XP002915897 ISSN: 0022-1554 pp. 774-776.

English Abstract for Ettmueller et al, EP472899 A1, filed Jul. 23, 1991, pp. 1-2.

* cited by examiner a  →  a' = a*n
b  →  b' = b/(n*m)
c  →  c' = c*m

PRECISE FLOW-ORIENTED MULTI-ANGLE REMISSION SENSOR

CROSS REFERENCE TO RELATED APPLICATIONS

This application is a National Phase Application of PCT/EP2004/014603, filed 22 Dec. 2004, which claims priority to DE103 61 058.8, filed 22 Dec. 2003.

The invention relates to a three-dimensional flow cell for aligning non-isometric particles in a liquid sample in two axes, a method of aligning non-isometric particles in a liquid sample, the use of a three-dimensional flow cell for aligning non-isometric particles in a liquid sample in two axes, a reflectance sensor built up from an optical unit, a sample analysis unit and a system control unit, and also a method of measuring the reflectance of a liquid sample containing non-isometric particles and the use of a reflectance sensor for measuring the reflectance of a liquid sample containing non-isometric particles, preferably a liquid sample in the form of a liquid pigment preparation containing non-isometric particles, at various process stages during the production, further processing and use of the sample, preferably the liquid pigment preparation.

Determining the reflectance of scattering preparations such as liquid samples which contain particles (dispersions) is an essential quality test. According to the prior art, the reflectance is determined with single-angle and multi angle color measuring instruments after a solid surface has been formed from these preparations.

Typical liquid samples which contain particles are liquid pigment preparations. During the production of liquid pigment preparations such as coating or enamel mixtures, pigment pastes, let-downs with white or other color mixtures, a reproducible color and hiding power of the mixtures is important. This reproducibility is ensured by means of regular product control during the production of the liquid pigment preparations, either visually or with the aid of spectroscopic methods. According to the prior art, the control is carried out by mixing the desired color mixtures, application to a substrate and drying, curing or baking and subsequent analysis of the colored layers obtained. Although this method is very accurate, it is very time-consuming.

A substantial time saving and, to some extent, better and reproducible results can be achieved by the measurement being carried out directly on the liquid pigment preparations, so that application of colored layers to a substrate and subsequent drying of the layers is not necessary. The reflectance measurement on liquid products has an additional area of application since, even in the case of "miscellaneous" products which are not immediately intended for the production of surfaces (as a coating or surface of a component), specific product and process properties can be determined from the reflectance and can be interpreted in relation to the disperse state (for example particle size distribution, form, concentration) or to material properties (for example refractive index, crystal modification, chemical composition).

In principle, all commercial color measuring instruments are suitable for this task. Each VIS sensor (VIS=visible, that is to say the range of visible light from 380 nm to 800 nm) operating in reflectance is likewise suitable for this purpose.

For example, EP-A 0 472 899 relates to a photometric measuring device for measuring the level of attenuation during the propagation of light in disperse systems. This device is built up from a through-flow cuvette for the sample to be examined, having at least one lateral opening for the optical connection of at least one optical waveguide. From a light source, an optical waveguide connection leads to the interior of the cuvette with the sample to be examined and from there to a light detector for generating a measured signal. A direct optical waveguide connection leads from the light source directly to the light detector for generating a reference signal. Furthermore, the photometric device comprises an evaluation device connected to the light detector.

WO 98/16822 relates to an analysis system for the analysis of the physical properties of coatings, pigment pastes or similar systems, which is built up from an apparatus for forming a film of the coating, pigment pastes and similar systems with a specific thickness, a light source for irradiating the coatings to be examined or the pigment paste to be examined or similar systems, interaction occurring between the light and the coating, the pigment paste or similar systems, a measured signal being generated; and an apparatus for recording the measured signal and also a detector connected to the apparatus for recording the measured signal.

The earlier priority German application with the file reference 103 30 641.2 relates to a reflectance sensor (embodiment (I)) built up from a) an optical unit (A), which comprises
   aa) a light source (Aa) in the form of a lamp, and
   ab) an optical waveguide (Ab) comprising fiber optics, at least one optical waveguide being a reference waveguide, b) a sample analysis unit (B), which comprises
   ba) a measuring window (Ba), and
   bb) a sample analysis cell (Bb),
   the optical unit being arranged on one side of the measuring window and the sample analysis cell being arranged on the other side of the measuring window, by said cell being pressed against the measuring window in such a way that a gap is formed between the measuring window and sample analysis cell, which gap the sample to be measured in the form of a liquid pigment preparation must traverse, considerable shear being experienced by the sample as it traverses the gap, and c) a system control unit (C) comprising detectors (Ca) for recording measured data and an evaluation device (Cb) connected thereto, at least one optical waveguide connection being led from the light source (Aa) to the measuring window (Ba) and from the measuring window (Ba) onward to the detector (Ca), to generate a measured signal (reflectance of the product), and at least one reference waveguide connection being led directly from the light source (Aa) to the detector (Ca) or from the measuring window (Ba) to the detector (Ca), to generate a reference signal (internal reflection).

This reflectance sensor is distinguished by high measurement accuracy and provides suitable measured data for determining the color and hiding power of liquid pigment preparations.

The analysis systems known in the prior art are suitable for the reflectance measurement of conventional liquid samples with isometric (that is to say uniform) particles, such as conventional coatings, uni-coatings, that is to say coatings in which colorants, for example organic or inorganic pigments, are added as coating components to the generally (but not necessarily) transparent binder of the coating in order to achieve decorative color effects, with isometric pigments or isometric other particles.

In addition, with effect pigments as supplementary coating components, further optical effects can be brought about. According to the present application, the group of effect pigments comprises metallic pigments and (the actual) effect pigments, for example interference pigments. Such coatings are designated effect coatings. A metallic mirror effect can be produced by means of metallic pigments, for example platelet-like aluminum flakes. Interference effects can be achieved by means of so-called interference pigments. These are normally platelet-like particles of a virtually transparent substrate material, for example mica, with a refractive index of the order of magnitude of the surrounding binder matrix, the outer surfaces being finished with an optically very highly refractive coating, for example of metal oxides. If metallic pigments and/or effect pigments are added to a coating (generally in addition to their colorants), then (desired) effects with considerable anisotropy are produced for an observer. This is because the lightness and chromaticity varies as a function of the viewing direction (goniochromatic effect). In the case of the effect pigments, a variation in hue also occurs. The optical properties, in particular the reflectance of liquid samples of such effect coatings, that is to say coatings which contain non-isometric particles, and other liquid samples which contain non-isometric particles, thus depend on the orientation of these non-isometric particles in the liquid sample.

For correct, reproducible measurements, in particular reflectance measurements of liquid samples which contain non-isometric particles, alignment of the particles before the measurements is thus necessary. In the case of needle-like particles, alignment in one axis is in principle sufficient. For the correct measurement of samples which contain platelet-like particles, for example metallic pigments and/or effect pigments, alignment in two axes is required. In the analysis systems known in the prior art for liquid samples containing particles, such alignment of the samples is not carried out.

It is therefore an object of the present application to provide an analysis system for the measurement, in particular reflectance measurement, of liquid samples which contain non-isometric particles, and to provide an apparatus for aligning non-isometric particles in a liquid sample, in particular in a liquid pigment preparation.

The liquid sample containing non-isometric particles concerns dispersions. Preferred liquid samples which contain non-isometric particles are liquid pigment preparations. Such liquid This object is achieved by a three-dimensional flow cell for aligning non-isometric particles in a liquid sample in two axes, comprising a feed zone for the sample containing particles to be aligned and an outlet for the sample containing particles aligned in two axes, a fluid element of the sample with the dimensions a, b, c being transformed in an expansion zone into a fluid element with the dimensions a×n, b/(n×m), c×m, a being the width, b the height and c the length of the fluid element and n and m being constants (degree of expansion) which depend on the geometry of the flow cell and which signify positive numbers $\geq 1$.

BRIEF DESCRIPTION OF DRAWINGS

Referring now to the figures, which are exemplary embodiments, and wherein the like elements are numbered alike:

FIG. 1 illustrates a flow cell in preferred embodiments.

FIG. 10 illustrates a preferred embodiment of an attenuator.

FIG. 11 illustrates a system preferably used for reflectance measurement.

The liquid sample containing non-isometric particles concerns dispersions. Preferred liquid samples which contain non-isometric particles are liquid pigment preparations. Such liquid pigment preparations are preferably coating or enamel mixtures, in the future, for example, pigment pastes, in special cases let-downs with white and black or other color mixtures or mixtures which contain non-isometric particles.

The three-dimensional flow cell according to the invention is suitable for use in an analysis system, preferably in a reflectance sensor, for measuring liquid pigment preparations which are present in various process stages in the production, further processing and use of the liquid pigment preparations. The analysis system containing the three-dimensional flow cell can be used, for example, to assess liquid pigment preparations during their production process or to assess the quality of the liquid pigment preparations during their use (for example for color matching in a coating installation) or for monitoring subsequent color changes of the liquid pigment preparations as a result of storage or shearing.

In this case, "color" is to be understood to mean the absorption+scattering of the pigment preparations. Typical "liquid pigment preparations" ("pigmented" preparation) are coatings and paints and also pastes, and coatings in general.

Non-isometric particles are to be understood, in particular, as effect substances, for example metallic pigments, that is to say aluminum flakes, or effect pigments or needle-like or platelet-like other particles (other particles is to be understood to mean those particles which do not fall under the particles explicitly listed above). Following processing, these non-isometric particles are present in an aligned form in the samples containing them. Quite particularly preferred liquid samples which contain non-isometric particles are thus effect coatings.

The principle of the two-dimensional alignment in the three-dimensional flow cell according to the invention is based on the fact that the fluid elements of a laminar flow are extended in two mutually orthogonal directions. If the three-dimensional flow cell according to the invention is used in a photometric device, in particular in a reflectance sensor, the two mutually orthogonal directions in which the fluid elements are extended run parallel to the measuring window.

Figure 1A:
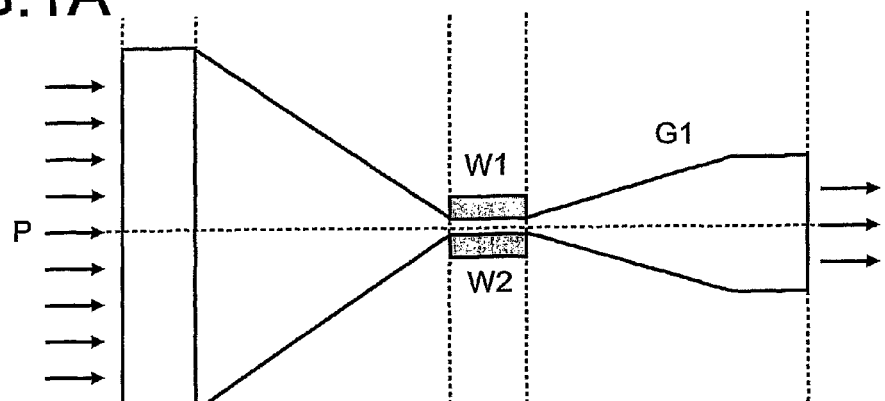
FIGS. 1a, 1b, and 1c are preferred embodiments of the flow cell in side view.
Figure 1B:
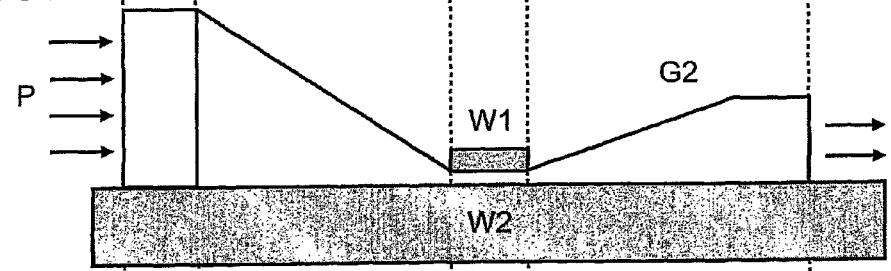
Figure 1C:
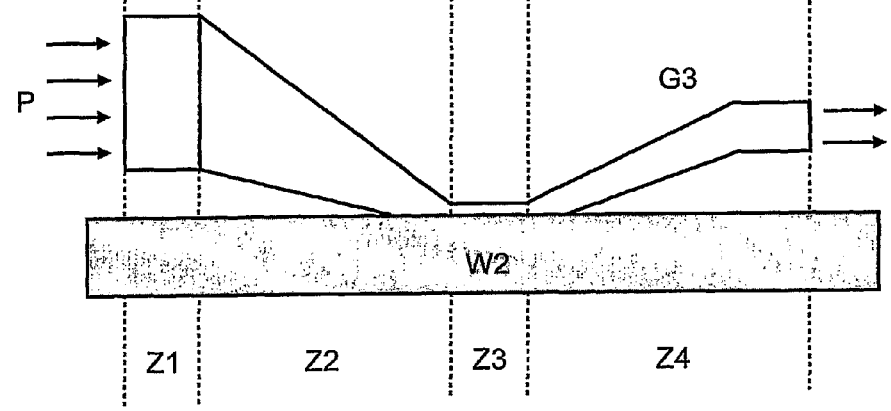
Figure 1D:
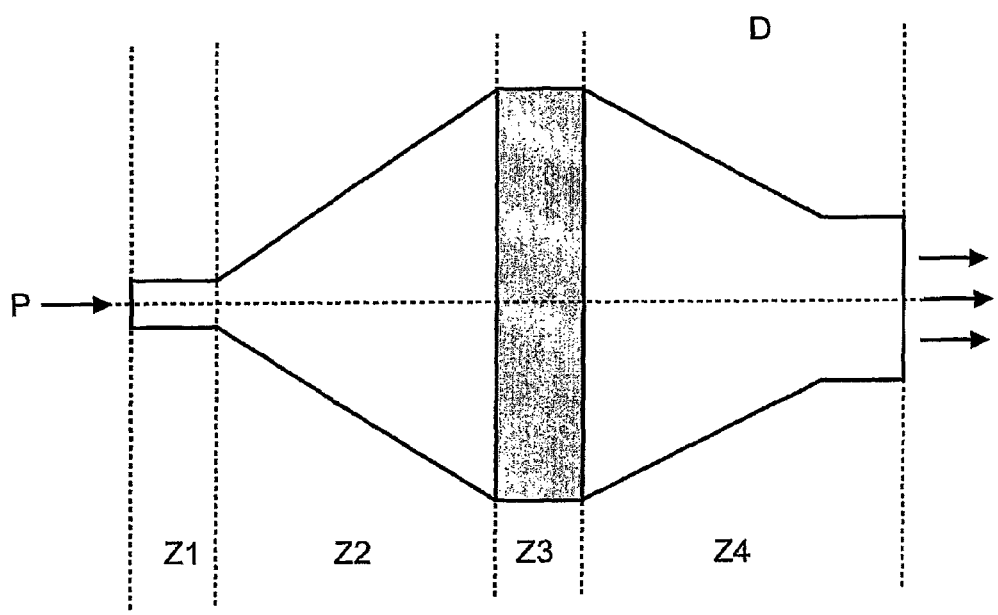
FIG. 1d is a plan view of the flow cells illustrated in FIGS. 1a, 1b, and 1c.
Figure 2:
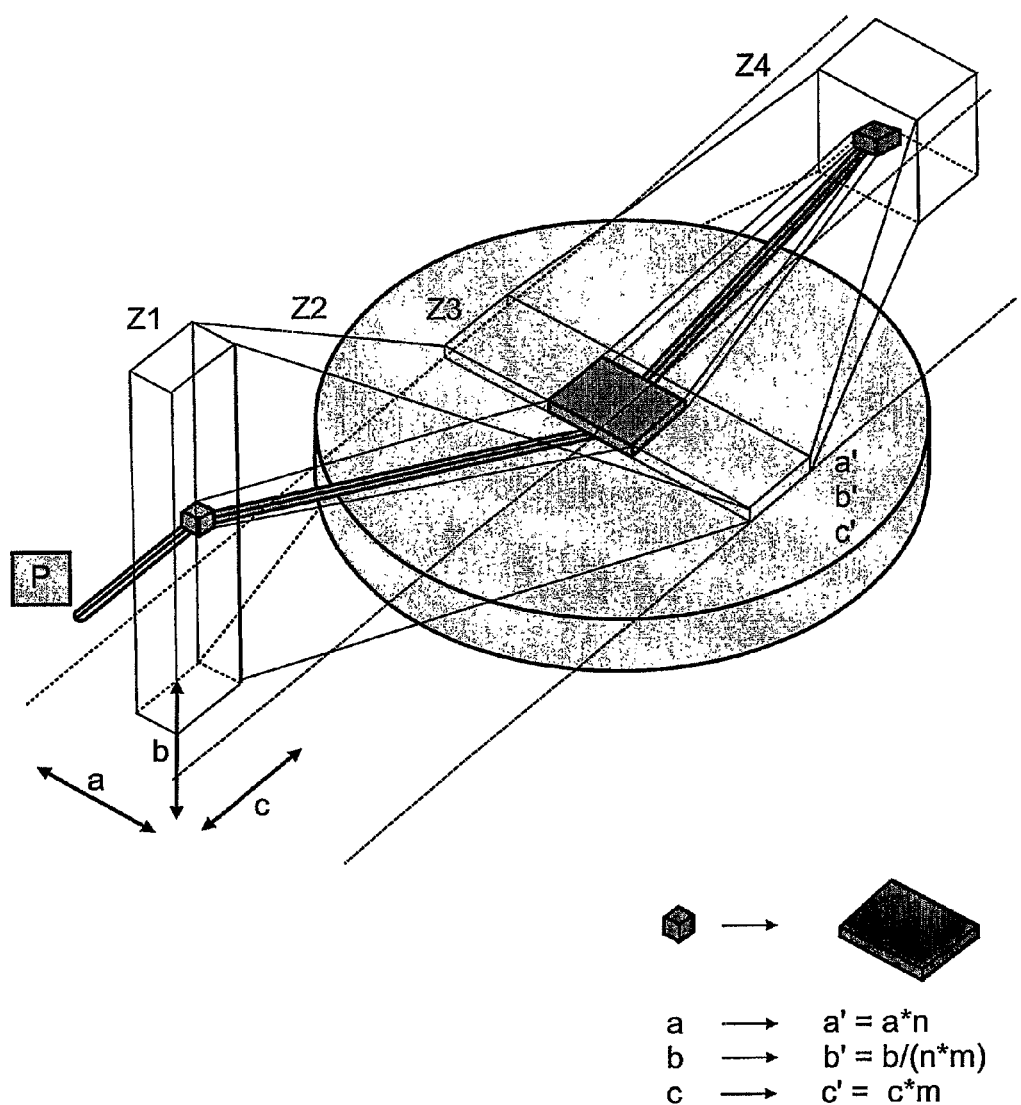
FIG. 2 illustrates deformation of a fluid element with dimensions a, b, and c in one embodiment of the flow cell.

FIG. 1 illustrates a flow cell in preferred embodiments. (FIGS. 1a, 1b, 1c, 1d), and FIG. 2 illustrates the deformation of a fluid element with dimensions a, b, c.

FIG. 1 illustrates a flow cell in preferred embodiments. FIGS. 1a, 1b, 1c are preferred embodiments of the flow cell in side view and FIG. 1d is a plan view of the flow cells illustrated in FIGS. 1a, 1b, 1c (identical for all three embodiments).

With reference to FIG. 1:

| | |
|---|---|
| Z1 | is the feed zone |
| Z2 | is the expansion zone |
| Z3 | is the measuring zone |
| Z4 | is the outlet zone |
| P | is the product flow |
| W1 | is measuring window 1 |
| W2 | is measuring window 2 |

| Side view | |
|---|---|
| G1 | is symmetrical geometry |
| G2 | is asymmetrical geometry |
| G3 | is folded geometry |
| D | means the plan view is identical for all |

FIG. 2 illustrates the deformation of a fluid element with dimensions a, b, c in one embodiment of the flow cell of the invention.

With reference to FIG. 2:

| | |
|---|---|
| Z1 | is the feed zone |
| Z2 | is the expansion zone |
| Z3 | is the measuring zone |
| Z4 | is the outlet zone |
| P | is the product flow |
| a | is the width of a fluid element before deformation in the flow cell |
| b | is the height of a fluid element before deformation in the flow cell |
| c | is the length of a fluid element before deformation in the flow cell |
| a' | is the width of the fluid element in the measuring zone, that is to say after deformation |
| b' | is the height of the fluid element in the measuring zone, that is to say after deformation |
| c' | is the length of the fluid element in the measuring zone, that is to say after deformation |
| n, m | represent the level of expansion |

The three-dimensional flow cell according to the invention comprises a feed zone, into which a liquid sample to be aligned, containing non-isometric particles, is introduced, an expansion zone, in which each volume element of the liquid sample is expanded in two axes, a measuring zone running in parallel, in which, for example, a reflectance measurement of the liquid sample aligned in two axes is carried out, and an outlet, from which the liquid sample containing non-isometric particles is led.

The liquid sample containing non-isometric particles is preferably carried as a laminar flow.

This generally laminar flow of the sample is rectified by means of flow rectification before entering the flow cell. Methods and apparatus for flow rectification are known to those skilled in the art. For example, flow rectification by means of a screen can be carried out.

The length of the expansion zone in the flow direction is configured in such a way that the opening angle of the bounding surfaces with respect to the average flow direction is if possible +/−15° to +/−45°, particularly preferably around +/−30°.

The outlet can generally be configured as desired. In principle, a feed can also be used as an outlet, so that, for example, a cell with two different cross-sectional shape changes can be used, which is used as a feed depending on the flow direction. Only the feed which is also used as a feed (that is to say is located upstream of the measuring zone) influences the alignment.

The sample is generally brought up to the connecting opening in the feed of the sample analysis cell with a hose or tube. From this generally circular connecting cross section, the sample stream must be matched to the entry cross section of the feed, which is generally high and narrow. This entry cross section generally comprises a flow rectification means, for example a screen or a grid. One advantageous design forms upstream of this cross section a similarly high but further chamber, in whose rear and/or side walls a plurality of part streams open at different heights. For this purpose, the sample feed stream is divided up into a corresponding number of part streams. One advantageous implementation of this design is the use of a plurality of bores with hose connectors in the sample cell bodies and distribution with a distributor comprising tubes or hoses (for example a Y piece or T piece from 1 to 2).

In the simplest form, the flow volume is symmetrical with respect to a mid-plane. In this case, however, use must ve made of a window which is rectangular and no longer than the measuring zone. In the preferred use of a large planar plate and a measuring cell that can easily be removed, the flow volume has to be modified, in that the inlet and outlet volumes are bent away from the plane of the plate relative to the measuring zone. One possible design in particular bends so far that the planar surface on the sensor side of the inlet/outlet volume coincides with the planar plate. A bend which goes even further is more advantageous, so that there is still a wedge of cell material between planar and flow volume (a wedge angle of 5° to 30° is advantageous, 15° to 25° is particularly advantageous), and only the measuring zone is bounded directly by the plate. As a result, only a small part of the plate is touched by the product.

If a fluid element of dimensions a, b, c is deformed (a width, b height, c length), because a flow cross section A, C is transformed into n×A, C×m, the result is a fluid element a×n, b/(n×m), c×m. The angles or their tangent in the a, b plane are varied by $1/(n \times n \times m)$, the angles in the c, b plane by $m^2/n$. An equivalent alignment in both axes is preferred, that is to say preferably (n×n×m)=(m×n×m), respectively n=m, and then both factors are $n^3$. Thus, for example with n=5, an entry cross section of A=4, B=25 is transformed into an outlet cross section of A=20, B=1 and aligned in both axes by the factor 125.

The achieved, defined alignment of the non-isometric particles, and also the defined deformation of the fluid element (alignment of macromolecules) can be used with various optical and non-optical measuring methods for determining further sample properties. In addition to the reflectance measurement known from colorimetry, other photometric arrangements (for example transmission, laser diffraction)

and imaging optical methods (for example image analysis, backscatter probes) can be employed.

n and m are the respective level of expansion of the fluid element. The absolute values for n and m depend, inter alia, on how severe the deformation of the fluid elements of a flow is intended to be. The severity of the deformation is in this case dependent on the intended application and on the size of the non-isometric particles in the liquid sample. In general, n is 1.5 to 7, preferably 2 to 5, particularly preferably 3 to 5, quite particularly preferably 4 to 5, the preferred values being suitable in particular when the flow cell according to the invention is used in photometric measuring devices, in particular reflectance sensors. When the flow cell according to the invention is used in image analysis, for example, other values for n can be preferred. m is preferably n, as already explained above.

The thermal motion, turbulence and rotational forces in the event of shear gradients counteract this alignment. Turbulence can be avoided by a suitable flow velocity to be determined without difficulty by those skilled in the art with a given geometry of the three-dimensional flow cell according to the invention. The rotational forces have a weaker effect the flatter the alignment is.

The deformation according to the invention is thus preferably carried out on a path which is sufficiently short to minimize the formation of a flow profile, but the decay of the alignment as a result of the thermal motion is at the same time sufficiently long for no sharp deflections of the flow to take place. In the adjacent parallel part (the measuring zone) as well the path length is chosen to be no longer than necessary, in order to minimize thermal diffusion and the formation of a flow profile. The parallel part merely has to be sufficiently long to accommodate completely the "measurement surfaces" which result from the beam cross section and angle of incidence. The measuring zone is preferably 2 to 10 mm, particularly preferably 4 to 8 mm, long. One advantageous variation is a second measurement at a greater distance, for example 10-20 mm, in order to register the extent of the decrease in alignment as a product property. Instead of varying the distance, a defined variation in the flow velocity can also be employed for this purpose.

The level of alignment itself depends to a first approximation on the expansion ratio, that is to say the flow velocity is selected such that still no turbulence occurs but is as high as possible, in order that the thermal disordering is minimized and the shear forces in the measuring gap (measuring zone) keep the surfaces that touch the product clean. With a given length of the measuring gap (measuring zone), a suitable flow velocity above the pressure loss is set (0.1 to 3 bar, preferably 0.5 to 1.5 bar). The volume flow is then measured, the flow velocity is calculated and checked for turbulence.

If the three-dimensional flow cell according to the invention is part of a photometric measuring device, then the liquid sample aligned in two axes strikes the measuring window (measuring zone) of the photometric measuring device directly at the end of the expansion zone.

A further subject is a method of aligning non-isometric particles in a liquid sample, the liquid sample flowing through a three-dimensional flow cell according to the present application, a fluid element of the liquid sample with the dimensions a, b, c being transformed into a fluid element with the dimensions a×n, b/(n×m), c×m, a signifying the width, b the height and c the length of the fluid element and m and n beign constants which depend on the geometry of the flow cell and which signify positive numbers $\geq 1$.

In the method according to the invention, it is preferable if $1/(n \times n \times m) = 1/(m \times n \times m)$. Preferred values for n have already been mentioned above.

Suitable liquid samples with non-isometric particles, and suitable non-isometric particles and suitable flow velocities at which the liquid sample flows through the three-dimensional flow cell have likewise already been mentioned above.

A further subject of the present application is the use of the three-dimensional flow cell according to the invention for the two-dimensional alignment of non-isometric particles in a liquid sample, preferably for the alignment of non-isometric particles in liquid pigment preparations.

The form of the flow cell, comprising a cross section-deforming feed zone, an expansion zone, a measuring zone running in parallel and an outlet has been described above. The mechanical construction of such a flow cell depends on the requirements specific to its use. For the preferred reflectance measurement, a particularly advantageous construction is implemented by a planar plate and a three-dimensional molding, which has a feed opening, a measurement opening for the fitting of the measuring window and an outlet opening. A suitable material is preferably metal or plastic, particularly preferably stainless steel and Teflon. This fabrication combines reproducible precision and easy cleaning.

The production of the flow cell is carried out in accordance with methods known to those skilled in the art, for example by boring, grinding or milling the flow path into a block of one of the aforementioned materials. Furthermore, the flow cell can be produced by injection molding if the material of the flow cell is suitable for injection molding.

A further advantageous fabrication technique is the press forming of plastics, preferably Teflon. This means that, by using a shaped plunger (tool), a basic volume can be pressed into a block and the necessary flow guidance can be achieved by simple, inserted displacement elements. The displacement elements are convex and can therefore be fabricated without difficulty using conventional methods.

The three-dimensional flow cell according to the invention can be used wherever alignment of non-isometric particles in liquid samples is desired. The three-dimensional flow cell according to the invention is preferably used in a photometric device for measuring the level of attenuation in the propagation of light in a liquid sample containing particles which are not isometric. Suitable liquid samples which contain non-isometric particles have already been mentioned above.

A further subject of the present application is thus a photometric measuring device for measuring the level of attenuation during the propagation of light in a liquid sample containing non-isometric particles, comprising a three-dimensional flow cell for aligning the particles in the liquid sample in two axes according to the present application.

The three-dimensional flow cell and preferred embodiments of the flow cell as well as suitable liquid samples containing non-isometric particles have already been mentioned above.

The physical principle of a photometric measurement is the determination of the intensity of light from a light source arriving at a detector as a function of the properties of a sample, for example of a disperse system. Depending on the manner in which light source, sample volume and detector are arranged and designed, the result is various dependencies of the measured signal on the scattering and absorption action of a solution, dispersion or emulsion.

The propagation of light or its attenuation is specifically a function of the dispersed suspension properties, more precisely of the specific scattering and absorption. Within certain limits, it is possible to use the optical properties to draw conclusions about the general dispersed properties, which in many cases can supply the basis for process control. Depending on the product, different requirements result on the type of measurement as regards the geometry and size of the measuring volume and the wavelengths used, for example transmission with infrared or reflectance with white light.

In general, the photometric measuring device can be operated in three operating modes:

Transmission:

Light passing through the measuring volume is measured (only possible in asymmetrical cell with two windows).

Quasi Backscatter:

The light which, as a result of the diffuse propagation of light in the dispersed medium, is scattered back in the irradiation direction again but enters a different phase, is measured (the sensor design is known to those skilled in the art, for example from EP-A 0 472 899; planar fitting in the measuring zone).

Reflectance:

The light which is reflected diffusely on the media-side interface of a transparent two-dimensional element terminating the light path, but generally not the reflection from the interface itself, is measured.

In the case of effect pigments, the diffuse reflection also has a maximum in the specular direction, but not as sharply as the mirror gloss of the interfaces.

Using the photometric measuring device according to the present application, the reflectance is preferably measured, that is to say the photometric measuring device according to the present application is preferably a reflectance sensor. The reflectance sensor is particularly preferably a highly accurate, flow oriented multi-angle reflectance sensor (flow oriented multi angle color sensor; Flomacs).

Figure 3:
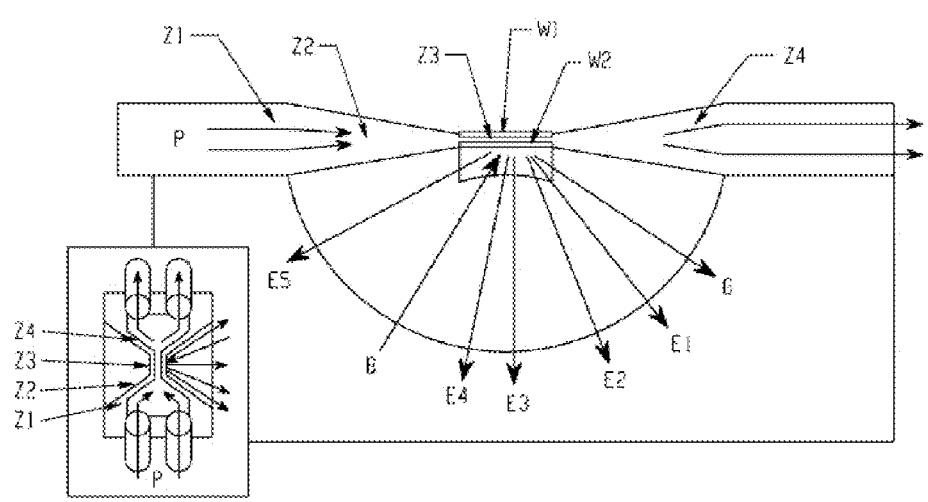
FIG. 3 illustrates the arrangement of the optical unit and sample analysis unit in relation to each other.

An example of a reflectance sensor is illustrated in FIG. 3, which depicts the arrangement of optical unit and sample analysis unit in relation to each other.

With reference to FIG. 3:

| | |
|---|---|
| B | is the illumination (=illumination fiber) |
| G | is the gloss |
| E1 | is receiver 1 (=receiving fibers) |
| E2 | is receiver 2 |
| E3 | is receiver 3 |
| E4 | is receiver 4 |
| E5 | is receiver 5 |
| P | is the product flow |
| Z1 | is the feed zone |
| Z2 | is the expansion zone |
| Z3 | is the measuring zone |
| Z4 | is the outlet zone |
| W1 | is measuring window 1 |
| W2 | is measuring window 2 |

In a preferred embodiment, the reflectance sensor is built up from a) an optical unit (A), which comprises aa) a light source (Aa) in the form of a lamp, and ab) an optical waveguide (Ab) comprising fiber optics, at least one optical waveguide being a reference waveguide, b) a sample analysis unit (B), which comprises ba) a measuring window (Ba), and bb) a sample analysis cell with three-dimensional flow cell (Bb), the optical unit being arranged on one side of the measuring window and the sample analysis cell with three-dimensional flow cell being arranged on the other side of the measuring window, by said cell being pressed against the measuring window in such a way that a gap is formed between the measuring window and sample analysis cell, which gap a liquid sample to be measured containing non-isometric particles must traverse, the liquid sample to be measured being led up to the gap through the three-dimensional flow cell, which is arranged upstream of the gap, in a special flow guide, and c) a system control unit (C) comprising detectors (Ca) for recording measured data and an evaluation device (Cb) connected thereto, at least one optical waveguide connection being led from the light source (Aa) to the measuring window (Ba) and from the measuring window (Ba) onward to the detector, to generate a measured signal (preferably reflectance of the product), and at least one reference waveguide connection being led directly from the light source (Aa) to the detector (Ca) or from the measuring window (Ba) to the detector (Ca), to generate a reference signal (internal reflection).

In the reflectance which is preferably measured, in this case the light which is reflected diffusely at the interface to the measuring window of a transparent two-dimensional element that terminates the light path is measured, but as a rule not the reflection from the interface itself (gloss). The latter forms an interfering background, which is generally between 1% and 0.001% of the white reflectance. This means that the direct reflection of the illumination at the plate should not be seen by the receiving fiber which receives the light scattered by the product, since this leads to a very high, undesired background component. However, the direct reflection can most certainly be received in a further fiber and can be used for the purpose of (additional or single) monitoring of the illumination intensity.

Colorimetry per se is prior art. If this procedure is explained here, then this is merely in order to clarify the fact that this sensor is suitable for all these methods. The reflectance measurement initially supplies the reflectance spectrum of the product, which is then referred to the reflectance spectrum of a white standard. From this normalized reflectance, the Lab values frequently used to describe color can then also be calculated. The reflectance measurement does not supply the hiding power directly or what are known as the absorption and scattering spectrum of a pigment preparation. However, these values can be determined by measuring the preparation in a non-covering layer thickness over black and over white and by measuring let-downs with white and let-downs with black.

For many products, considerable advantages in terms of cost result if the properties of the samples can already be determined on the liquid preparation, in particular in the case of coatings. The measurement of the reflectance with the measuring device according to the invention is particularly suited to this. In the following text, the particularly preferred reflectance sensor will be explained in more detail.

a) Optical Unit (A)

The optical unit, according to the invention, has one or more light sources (Aa) and all of the fiber optics (Ab).

The light source must have a sufficient intensity and luminous density in order that a spectrometer can be operated in the range from 50 to 2000, preferably 100 to 600 ms integration time. Furthermore, the spectrum of the lamp must be such that, in the case of white, all the wavelengths of the spectrometer are driven from 5% to 95%, preferably 10% to 95% in the case of a lamp without correction and from 25% to 95% in the case of a lamp with correction. In this case, the highest possible percentages (in particular 95%) are particularly desirable. By using color filters, the spectrum of the lamp can be improved further. These filters are only able to "bend straight" lamp spectra which are smooth.

Individual maxima that run very steeply, such as are possessed in great numbers by many gas discharge lamps, cannot be corrected.

Furthermore, chronological and spatial homogeneity is desirable. If a halogen lamp is used, it is preferably improved by defocusing and by a diffuser. The aperture angle of the fiber (=optical waveguide) should be "filled with light" homogeneously. The fiber should not be curved too sharply. All improvement measures are made at the cost of the intensity.

The light source is a lamp, for example LEDs, gas discharge lamps (for example XBO) and lamps with incandescent filaments being suitable; a halogen lamp is preferred. A lamp with integrated shutter is particularly preferred. However, it is also possible to use other lamps which preferably have a spectrum, so that a dynamic of about 3 or less is achieved. At the same time, the lamp should exhibit low intensity fluctuations and sufficient brightness. The halogen lamp preferably used generally has a stabilized DC power supply unit.

Lamps with shutter operation are particularly preferred. In the case of sluggish light sources, such as incandescent filaments (halogen) or gas discharge, this is achieved with a mechanical or, for example, optoelectronic shutter (possibilities known to those skilled in the art); in the case of faster light sources such as diodes or flash lamps, this is implemented by the electrical drive system.

According to the present application, preference is given to an arrangement in which a compensation filter is arranged behind the lamp, preferably halogen lamp. In this case, "behind the lamp" is to be understood to mean that the compensation filter is arranged after the lamp following the course of the light beam from the lamp. The compensation filter used in the preferred embodiment linearises the spectrum of the lamp in such a way that the difference between the highest and lowest intensity of the light emitted by the lamp is at most 4, preferably 3 to 4 and not 10 to 20, as is usual in the prior art. This is achieved with multilayer filters of commercially available filter glasses.

In a further preferred embodiment, an IR blocking filter, a condenser and a diffuser are arranged behind the lamp, preferably halogen lamp, between lamp and compensation filter if a compensation filter is used, which is preferred. Once again, "behind the lamp" in the sense of the present application means after the lamp, following the light beam. The IR blocking filter is used to reduce the thermal loading which acts on the sample, the optical waveguides, the compensation filter and other units of the reflectance sensor from the lamp. The condenser is used to focus the light from the lamp on the input of the fiber optics. The diffuser is used to achieve a structure-free, uniform course of the brightness of the light from the lamp over the location and the aperture angle of the optical waveguides. Suitable embodiments of IR blocking filters, condensers and diffusers which are suitable for the reflectance sensor according to the invention are known to those skilled in the art.

The shutter preferably integrated into the lamp according to the invention is preferably an electromechanical shutter which can darken the illuminating fiber completely. The darkening by the shutter is used to measure the dark current.

This means that the shutter interrupts the light stream from the lamp to the illuminating fiber. This is necessary in order to measure the dark current of the spectrometer (this current always flows and leads to an indication even when there is complete darkness), which must be subtracted from the measured value of the product. The spectrometer is erased by reading, but only to about 99%, so that a remnant of the last measurement remains in the spectrometer and distorts the first dark measurement. Starting from the second successive dark measurement, the value is then undistorted.

The fiber optics of the reflectance sensor according to the invention comprises optical waveguides (=fibers), depending on the design. These fibers are one or more reference fiber(s), a plurality of receiving fibers and one or more illuminating fiber(s). In principle, embodiments are also possible which do not have any reference fiber(s). However, the fiber optics normally comprise at least one reference fiber. The at least one reference fiber generally leads directly from the light source (Aa) to the detector (Ca). However, it is also possible for at least one reference fiber to lead from the measuring window (Ba) to the detector (Ca).

In principle, the reflectance optics therefore comprises optical waveguides (fibers), possibly lenses, aperture stops, diffusers, and a common front element, which is penetrated both by the light from the illuminating fiber and by the light which the product scatters back (reflectance) on the way to the receiving fiber. This front element is advantageously a planar plate of transparent material, but in principle can also be implemented as a prism, lens, rod, cylinder or fiber, in an extreme case even as an air pad with or without film.

Since the spectrometer itself generally has a short receiving fiber, in a further embodiment the spectrometer can be connected to the detector directly without the use of further optical waveguides.

As necessitated by the material, the fibers normally used have an opening angle of +/−10-15° (divergence). By means of aperture stops and lenses, the beam path can be transformed to other cross sections and other divergent or convergent opening angles. It is therefore possible to illuminate and to observe a measuring spot of defined size with a beam path with a small opening angle (0.5°-5°, preferably 1°-3°, particularly preferably about 2°). The gloss reflected from the interface has the same opening angle as the illumination and is no longer received by observation optics if the angle between gloss angle and observation angle is greater than the sum of the aperture angles. Because of the limited luminous density of the fibers and the size of the measuring spot, a defocusing allowance must further be taken into account in the differential angle. In the example of +−2° opening angle, 800/600 μm fiber diameter, 10 mm lenses with 15 mm focal length, 3 mm measuring spot, 5 mm illumination spot and 70 mm working distance, it is possible to measure from about a 10° differential angle. The opening angle is limited either by aperture stops or by the lens diameter. The circular beam cross section is stretched to form an oval spot by means of the inclination (1/cos(angle)). It is therefore necessary to take care that, at larger angles, the measuring spots are still located completely in the illumination spot. A safety margin of 1-2 mm is advantageous.

It has been found that the concentration dependence is low at low penetration depths if the illumination spot is made larger than the measuring spot (compatible with a short shearing gap length according to the invention). The illumination spot is therefore preferably larger than the measuring spot. The diameter of the illumination spot is particularly preferably 4 to 20 mm, particularly preferably 5 to 10 mm, and the diameter of the measuring spot is 1 to 10 mm, particularly preferably 2 to 5 mm. The reflectance sensor according to the invention is thus suitable in particular for exact reflectance measurements on liquid pigment preparations.

The optical waveguides are preferably fibers of 100, 200, 400, 600 or 800 μm fiber diameter or fiber bundles, for example as firmly mounted on the spectrometer. The fiber used as a reference waveguide particularly preferably has a matched, preferably smaller diameter than the other optical waveguides, since the lamp used, preferably halogen lamp, itself has a high light intensity.

In order to achieve high measuring accuracies, the optical waveguides in a preferred embodiment of the method according to the invention are mechanically protected. For the purpose of mechanical protection, the optical waveguides are guided in protective tubes and are supported over their entire length by means of a supporting frame. The protective tubes are generally made of conventional materials known to those skilled in the art, for example metal or polymer. The supporting frame is preferably a metal frame, to which the optical waveguides are fixed by means of conventional fixing materials, for example cable ties or adhesive tape.

In a preferred embodiment of the reflectance sensor according to the invention, the reference waveguide is led via an attenuation element, that is to say a precise spacing element with incorporated diffuser, in order to maintain the full aperture angle.

The illumination and observation of the interface on the sample side of the measuring window is generally carried out by means of the abovedescribed fiber arrangements, that is to say at the point of intersection of the optical axes of the fibers (preferably taking account of the offset of this axis at the entry into the measuring window). As described, the "natural" beam path of a fiber (optical waveguide) is preferably transformed by optical elements in order to achieve an illumination or measuring spot with the desired properties (size and homogeneity of the spot, aperture angle of the beam path). During the design, the following considerations should be applied:

The illuminating beam is reflected geometrically (that is to say in a directed manner) at the inner (possibly mirrored) interface and at the interface on the sample side of the measuring window. The reflection angle is called the gloss angle in colorimetry. No information about the reflectance of the sample is hidden in this reflectance.

If the metallic and the effect pigments are aligned parallel to the measuring window (analogously to an alignment parallel to the coating surface in an applied coating), anisotropic scattering takes place, which can be very differently pronounced. The maximum reflectance likewise takes place at the gloss angle, that is to say the reflections from the interface and the pigments are superimposed at the gloss angle. In the case of larger angles in relation to the gloss angle, the reflectance decreases in all directions but not to the same extent.

By contrast, the reflections have exactly the beam cross section and the aperture angle of the illumination. They can therefore be masked out by means of appropriately angle-selective observation and the reflectance of the sample (containing non-isometric particles) can be measured closer to the gloss. In dry colorimetry (prior art), this is generally an angle of 15° from the gloss toward the illumination. In principle, any desired small angles are possible, but not exactly 0°. Angles from about 5° away from the gloss angle (irrespective of in which direction) are capable of practical implementation technically.

Furthermore, measurements are also made at larger angles with respect to the gloss and also at steeper (smaller) or flatter (larger) illumination angles. It is always necessary to take care that the illuminating or measuring spot broadened by the shallow angle of incidence still remains in the measuring zone suitable for this purpose.

Furthermore, in the case of measurement on liquid samples, as described, preferably using a planar plate, the angular range which can be handled easily is also restricted by the reflections, which increases at shallow angles (as far as total reflection).

Examples of the selection of practical angles are listed further below.

It is thus generally necessary to optimize the high dynamics between observation angles close to the gloss and remote from the gloss (called the FLOP), which can reach the factor 200, by means of a variable or fixed intensity adaptation (by means of filters, attenuators and/or diffusers) of the individual channels, in order to achieve good level control in all channels. Alternatively or additionally, the measurement can be carried out at two or more different integration times, the light source preferably then being monitored over two or more different observation beam paths in order to measure the reference intensity with adequate level control. A plurality of parallel reference fibers with their own spectrometers is one possible design, a plurality of parallel reference fibers with their own shutter, which are then led together onto a spectrometer, is another alternative.

The preferred embodiments described here can be improved in terms of their crosstalk behavior if the side of the measuring window facing away from the product is made nonreflective, which is preferably done. This is also advantageous in order to minimize the reflections at the shallow observation angles.

In principle, various fiber arrangements are conceivable in the reflectance sensor according to the invention. Preferred fiber arrangements can be determined by those skilled in the art on the basis of the following criteria, it being necessary to take into account the fact that the liquid sample contains non-isometric particles:

A) Sensitivity to light: this has an effect on the necessary integration time of the sensor. Since the light output of the lamp is limited, as are the fiber diameter and likewise the sensitivity of the sensor, integration times between 50 and 2000 ms are typical. 100 to 600 ms are desirable. Longer integration times than 2000 ms are not beneficial, since then the dark current component rises and the signal error increases. The resulting longer measuring time is not beneficial (even more so if the measurement is repeated many times in order to minimize the error). The cooling of the sensor in order to reduce the dark current is very complicated.

B) Stability: A reproducibility of 0.05 to 0.2% of the reflectance is particularly preferred. Depending on the color, this corresponds to a dE of 0.02 to 0.08. (With the reflectance sensors known in the prior art, a reproducibility of 1 to 10% is achieved when measuring liquid samples.) The timescale is in this case in the minutes range, that is to say the deviation between two immediately successive measurements (with the same product or as a comparison with the product type), or the time interval between two calibrations (e.g. 24 hours), and also the long-term stability resulting from repeated calibration. Critical factors here are the ageing of the optical parts and fibers, mechanical displacement, shrinkage and swelling of the materials, creep phenomena and fatigue arising from alternating thermal load, the repeatability of mechanical positioning during calibration, ageing and replacement of the light source, wear of the surface with which the product makes contact. The various geometries are not sensitive to the same extent with respect to these factors.

C) Crosstalk damping: This means, firstly, the uncontrolled amount of light getting from the light source into the receiving fiber when an ideal black product is present on the front plate (measuring window), as compared with the amount of light reflected by the reference white (100%, e.g. white standard, white paste). Here, ratios of 10% ($10^{-1}$) to 0.01% ($10^{-4}$) or better can be achieved. Dark products exhibit about 1% reflectance. Although the background can be subtracted by computation, this is at the cost of accuracy. Crosstalk damping which begins at a factor 30, preferably at a factor 100, below the reflectance of the product is preferred. Secondly, this also means the "resolution" of the flop, that is to say the light scattered in one direction must not get by uncontrolled reflection into fiber optics which are intended to detect the light from another angular range.

D) Concentration dependence: Colorimetry for coatings and pigment preparations, within certain limits, is independent of the concentration of the pigments. This is true as long as the layer thickness tested provides coverage. In the case of conventional color measuring instruments, in the usual area of application with covering products, there is no concentration dependence, that is to say no dependence of the reflectance on the penetration depth. Surprisingly, some geometries described here exhibit a concentration dependence in some regions.

The fiber arrangement (reflectance geometry) will generally be configured by a front element being defined as the starting point of an optical arrangement. The front element in the reflectance sensor according to the invention is the measuring window (Ba). In general, the material, refractive index, thickness and planarity of the measuring window are definitive. Thicknesses of the measuring window of in general 1 to 20 mm, preferably 4 to 10 mm, particularly preferably 6 to 8 mm, are practical. The diameter is preferably 40 to 100 mm, particularly preferably 50 to 80 mm. Suitable materials are all optically transparent materials, for example glass (quartz), semi-precious stones (sapphire) or diamond. In this series, the increasing hardness is beneficial, the increasing price and the increasing refractive index are not beneficial (more reflections). An internal antireflection coating is advantageous for all. The central normal to the measuring window (the plate) forms a reference system (plate axis).

In one embodiment of the reflectance sensor according to the invention, illumination is provided at only one angle and measurements are made at a plurality of reflectance angles, preferably three to seven. Particularly preferably, measurements are made simultaneously with a plurality of spectrometers, preferably three to seven, and also one spectrometer to provide a reference for the light source. This means that the fiber optics in the reflectance sensor according to the invention in one embodiment have one illuminating fiber and a plurality of receiving fibers, preferably three to seven.

All the fibers associated with one illuminating direction (receiving fibers, illuminating fibers) lie in one plane, which is perpendicular to the measuring window, since the alignment is carried out parallel to the measuring window. Differing from a reflectance sensor for isometric pigments, this plane cannot therefore be inclined toward the measuring window in order to improve the crosstalk damping. The latter is therefore set only by the limitation of the aperture angle and the reduction of the internal reflection. The angle of this plane with respect to the flow direction can be chosen freely. The angle 90° (that is to say transverse) is preferred, since in this way the measuring and illuminating spots are pulled apart transversely with respect to the flow direction, and the shearing edge can in this way remain quite short.

Figure 4:
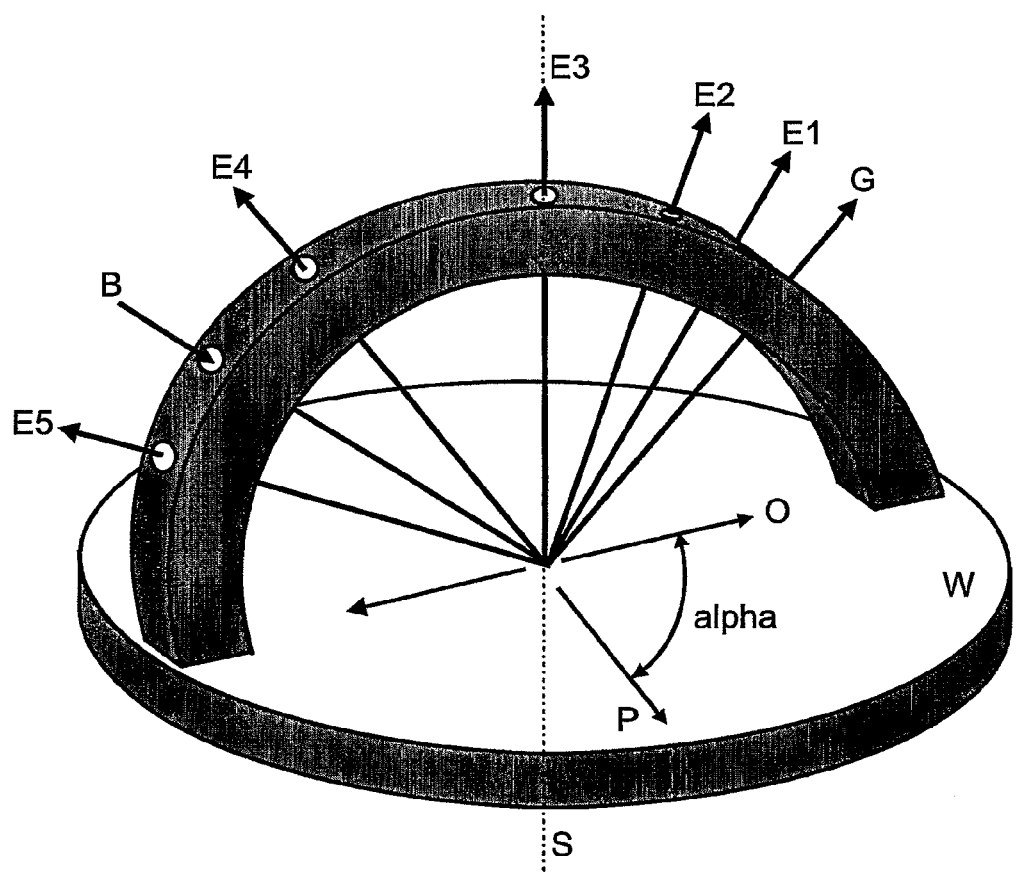
FIG. 4 illustrates optics with illumination at one angle and measurement at a plurality of reflectance angles.

One example of such optics is illustrated in FIG. 4, which shows the illumination at one angle and measurement at a plurality of reflectance angles.

With reference to FIG. 4:

|    |              | Angle w.r.t. the gloss | Angle w.r.t. the normal |
|----|--------------|------------------------|-------------------------|
| B  | Illumination | 90°                    | 45°                     |
| G  | Gloss        | 0°                     | −45°                    |
| E1 | Receiver 1   | 15°                    | −30°                    |
| E2 | Receiver 2   | 25°                    | −20°                    |
| E3 | Receiver 3   | 45°                    | 0°                      |
| E4 | Receiver 4   | 75°                    | 30°                     |
| E5 | Receiver 5   | 105°                   | 60°                     |

Figure 5:
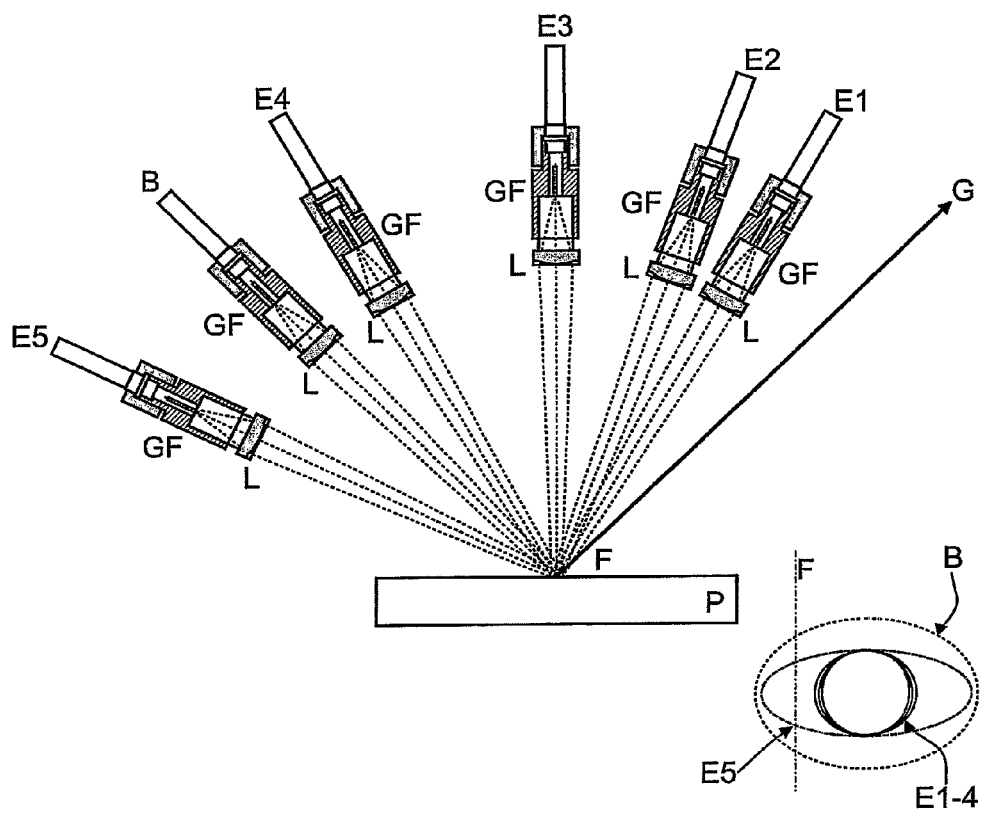
FIG. 5 illustrates the light beam path with illumination at one angle and measurement at a plurality of reflectance angles.

W Measuring window
S Normal to the plate/to the measuring window
O Optical axis
P Product flow
alpha Angle between optical axis and product flow An example of the associated beam path is illustrated in FIG. 5, which depicts illumination at one angle and measurement at a plurality of reflectance angles.

With reference to FIG. 5:

|    |              | Angle w.r.t. the gloss | Angle w.r.t. the normal |
|----|--------------|------------------------|-------------------------|
| B  | Illumination | 90°                    | 45°                     |
| G  | Gloss        | 0°                     | −45°                    |
| E1 | Receiver 1   | 15°                    | −30°                    |
| E2 | Receiver 2   | 25°                    | −20°                    |
| E3 | Receiver 3   | 45°                    | 0°                      |
| E4 | Receiver 4   | 75°                    | 30°                     |
| E5 | Receiver 5   | 105°                   | 60°                     |

F Focus
P Product flow
L Lens
GF Glass fiber

The result of this is that illumination is preferably carried out at 45° to the normal, and observation is carried out at various angles, that it is to say at −40° to −30° (close to the specular reflection), in the range −20° to +30°, but also at relatively shallow angles such as 55° to 65°. In order to achieve high angular resolution, it is also advantageous to set the aperture angle range of the fibers of +/−12° by means of optics to a maximum of +/−5, preferably at most +/−2 or less. In this case, with available fibers in the range from 100 to 800 μm and conventional lenses of 10-15 mm diameter (range 2 to 40 mm), measuring spots in the range from 1 to 10 mm can be achieved, which is compatible with the use of the shearing gap required.

In a further preferred embodiment, the reflectance measurement is carried out at various (a plurality of) illumination angles. The reflectance sensor according to the invention thus preferably has a multi angle measuring device, it being possible for the reflectance to be measured at a plurality of illumination angles (multi angle reflectance sensor).

When implementing a plurality of illumination angles on an analysis cell, it may be necessary, for reasons of a lack of space, to provide each illumination direction with its own plane, that is to say different angles with respect to the flow direction. In this case, it is advantageous if the flow direction forms the bisector to the two planes. The angles preferably lie in the range from +/−20° to +/−70°, particularly preferably +/−50° to +/−60°.

Figure 6:
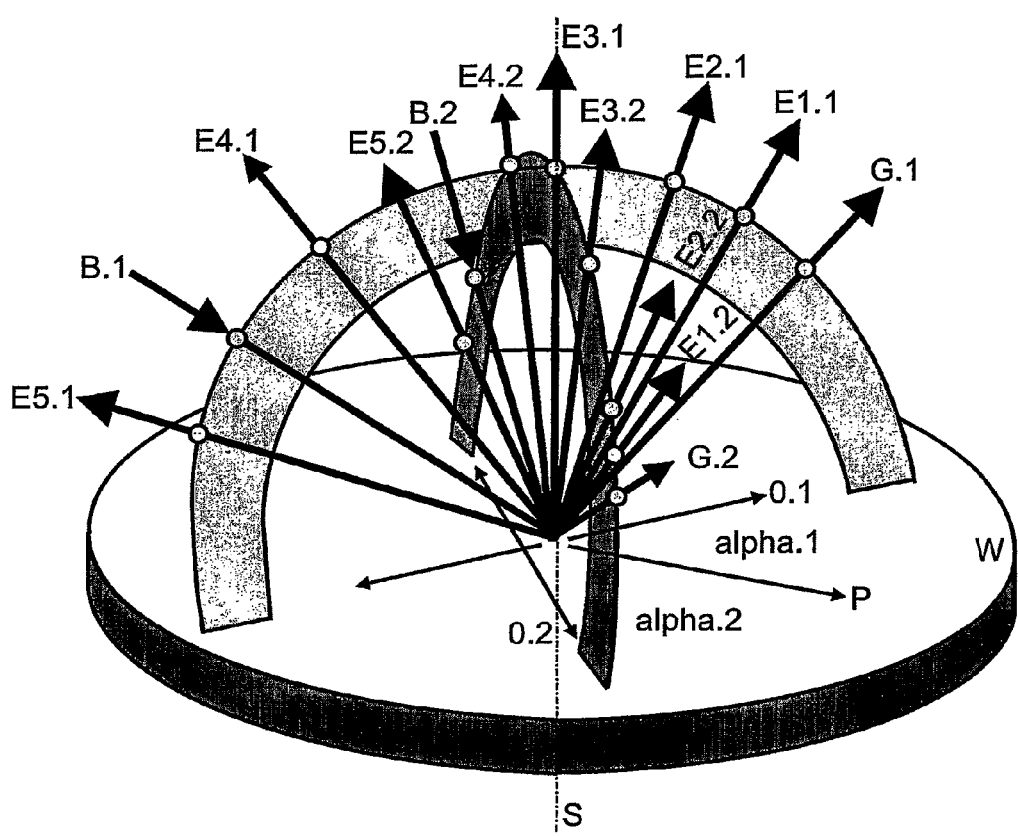
FIG. 6 illustrates optics with illumination at a plurality of illumination angles.

One example of such optics is illustrated in FIG. 6, which depicts illumination at a plurality of illumination angles.

With reference to FIG. 6:

|  |  | Angle w.r.t the gloss | Angle w.r.t the normal |
|---|---|---|---|
| Observation group 1 | | | |
| B.1 | Illumination | 90° | 45° |
| G.1 | Gloss | 0° | −45° |
| E1.1 | Receiver 1 | 15° | −30° |
| E2.1 | Receiver 2 | 25° | −20° |
| E3.1 | Receiver 3 | 45° | 0° |
| E4.1 | Receiver 4 | 75° | 30° |
| E5.1 | Receiver 5 | 105° | 60° |
| Observation group 2 | | | |
| B2 | Illumination | 120° | 60° |
| G2 | Gloss | 0° | −60° |
| E1.2 | Receiver 1 | 15° | −45° |
| E2.2 | Receiver 2 | 25° | −35° |
| E3.2 | Receiver 3 | 45° | −15° |
| E4.2 | Receiver 4 | 75° | 15° |
| E5.2 | Receiver 5 | 105° | 45° |

W Measuring window
S Normal to the plate/measuring window
O1 Optical axis observation group 1
O2 Optical axis observation group 2
P Product flow
alpha1 Angle between optical axis 1 and product flow
alpha2 Angle between optical axis 2 and product flow Some particularly advantageous embodiments of a construction of a reflectance sensor in which a plurality of illumination angles (and a plurality of receiving angles) are implemented are discussed in the following text.

I. In order to carry out a measurement of liquid samples containing non-isometric particles at various illumination angles, it is possible to carry out measurements in a plurality of measuring cells each having one reflectance sensor, through which the sample flows in parallel or sequentially.

II. However, it is more cost-effective to implement a plurality of illumination angles in one of measuring cell (reflectance sensor), that is to say with a single optical unit. This is possible with a plurality of individual light sources or multiple light sources (shutters are likewise preferably present) and a corresponding number of receiving paths and spectrometers. In this case, a substantial prolongation of the measuring time can be avoided by the measurements being carried out in such a way that all the spectrometers determine their dark current simultaneously. In further embodiments, it is possible for the light paths to be arranged in a plurality of mutually crossing planes and/or for individual receivers to be used many times.

Switching on various illumination paths with different angles sequentially and measuring at one observation angle is also possible, or combinations of these methods.

In principle, in a multi angle measuring device according to the invention, various variants are conceivable, for example illumination angles<45° up to illumination angles of at most 65° (with respect to the normal), preferably at most 60°, and angles of the receiving fibers from about 10° from the gloss to at most 65° (with respect to the normal), preferably at most 60°.

Taking note of these relationships, the optimum for an application can be determined experimentally in a straightforward manner by those skilled in the art.

In order to connect the optical waveguides (=fibers) to the light source and the detector, commercially available SMA plugs are generally used.

In a particularly preferred embodiment, the photometric measuring device according to the invention, preferably a reflectance sensor, additionally has at least one of the following features:

ac) arranged behind the lamp is a compensation filter, which linearises the spectrum of the lamp in such a way that the difference between the highest and lowest intensity of the light emitted by the lamp is as small as possible, for example a maximum of a factor 4, ad) arranged behind the lamp—between lamp and compensation filter if a compensation filter is used—are an IR blocking filter, a condenser and a diffuser, ae) the optical waveguides are guided in protective tubes and are supported over their entire length by means of a supporting frame, af) the reference waveguide is led via a precise spacing element with incorporated diffuser, and attenuated in a defined manner.

The individual features according to ac), ad), ae) and af) have already been specified in detail above. The photometric measuring device according to the invention, preferably a reflectance sensor, particularly preferably additionally has at least the features ac) and ad), quite particularly preferably at least the features ac), ad) and ae), and in particular the features ac), ad), ae) and af).

b) Sample Analysis Unit (B)

The sample analysis unit (B) comprises a measuring window (Ba) and a sample analysis cell with a three-dimensional flow cell (Bb).

The measuring window (Ba) is generally a planar plate. Suitable materials for the planar plate are all optically transparent materials, for example glass (quartz), semi-precious stones (sapphire) and diamond. The planar plate generally has a thickness of 1 to 20 mm, preferably 4 to 10 mm, particularly preferably 6 to 8 mm, and a diameter of generally 40 to 100 mm, preferably 50 to 80 mm. The planar plate is inserted into a block, preferably a metal block, for example of titanium or stainless steel, so as to be resistant to pressure and solvent. For this purpose, the planar plate is bonded in, for example, or inserted into the block by another joining technique. In one embodiment of the present invention, a planar plate of sapphire is vapor-coated with gold for the purpose of pressure-resistant and solvent-resistant insertion. The measuring window in itself preferably protrudes by a few μm, generally 0 to 100 μm, preferably 0 to 50 μm, particularly preferably 10 to 20 μm. The measuring window is generally vertical, so that simple filling of the sample analysis unit with the liquid sample containing non-isometric particles which has previously traversed the three-dimensional flow cell (Ba), and simple outlet of solvent, are possible. The measuring window is preferably circular. The metal block preferably forms a drip edge, in order specifically to form drops of the liquid samples used at this point, in order that these do not reach sensitive points of the reflectance sensor.

On the other side of the measuring window (that is to say on the other side of the measuring window from that of the optical unit), the sample analysis cell is arranged, by the latter being pressed against the measuring window in such a way that a gap is formed between the measuring window and sample analysis cell, which gap a liquid pigment preparation to be measured has to traverse, shearing of the sample taking place as it traverses the gap. The shearing is preferably achieved by the pressure loss in the gap preferably being 0.1 to 3 bar over 1 to 15 mm length, particularly preferably 0.5 to 1.5 bar over 2 to 8 mm length. The fact that the sample analysis cell is pressed against one side of the measuring window (and can be removed) permits the optical unit and, if necessary, the measuring window, to be cleaned and calibrated easily.

The sample analysis cell is preferably a block, from which the three-dimensional flow volume described above has been machined out or has been formed by the fabrication methods described above.

A particularly important dimension is the height of the shearing gap, that is to say the height of the measuring zone. This dimension affects three important properties:

i) the level of alignment (dimensions of the measuring zone, see the discussion of the dimensions a, b, c, n, m)

ii) the shear loading (keeping the measuring window clean, the pressure loss is proportional to the sample viscosity and to the length of the measuring zone and approximately inversely proportional to the square of the gap height)

iiia) in the case of measurements in reflectance, the layer thickness does not necessarily have to provide coverage, but it is simpler and more accurate if this boundary condition is maintained (for example, as is also usual in dry colorimetry). The hiding power is preferably >96%, particularly preferably >99%. Depending on the sample characteristics, this gives the minimum layer thicknesses (and therefore the gap height). In most products, these lie between 0.2 and 2.5 mm, normally between 0.5 and 1.5 mm.

iiib) In the case of measurements in transmission, the layer must be sufficiently thin for an amount of light which can still be handled easily to pass through. For the image analysis or extinction number, more than 50% of the light should pass through, for integral transmission measurements, the transmission layer (and therefore the gap height) should be between 0.02 and 0.5 mm, preferably between 0.05 and 0.2 mm. The upper limit is not critical in this case, but the lower limit certainly is, since layer thicknesses of less than 0.05 mm are difficult to handle.

iiic) In the case of other measurements, the layer can as a rule be designed merely in accordance with the criteria 1 and 2.

The gap height is generally between 0.05 and 5 mm, preferably between 0.2 and 2.5 mm, particularly preferably between 0.5 and 1.5 mm.

According to the present invention, the liquid sample containing non-isometric particles is brought up to the shearing gap (=measuring zone) in a special flow guide. This special flow guide is achieved by the liquid sample traversing a three-dimensional expansion zone according to the present application, and an adjoining measuring zone (shearing gap). As they traverse, the particles are aligned in two mutually orthogonal directions, which both run parallel to the measuring window. Here, a fluid element belonging to the liquid sample and having the dimensions a, b, and c is transformed into a fluid element having the dimensions a×n, b/(n×m) and c×m, a being the width, b the height and c the length of the fluid element and n and m being constants which depend on the geometry of the flow cell and which signify positive numbers $\geq 1$. Preferred embodiments of the three-dimensional flow cell and values for n and m have already been mentioned above. When selecting the cross sections and expansion coefficients (a, b, c, n, m), a suitable shearing gap (=measuring zone) must be set.

Figure 7:
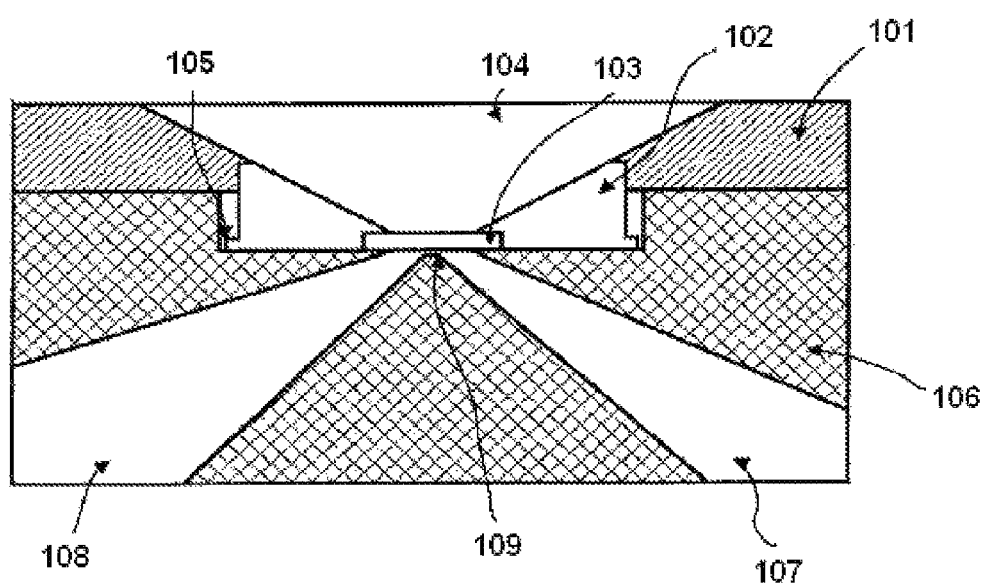
FIG. 7 is a side view of the reflectance sensor with three-dimensional flow cell for measuring liquid samples containing non-isometric particles.

FIG. 7 illustrates a preferred embodiment of a reflectance sensor having a sample analysis unit (B) for the reflectance measurement of liquid samples containing non-isometric particles, comprising the measuring window (Ba) and the sample analysis cell with three-dimensional flow cell (Bb) and also a holder for the fiber optics (Ab) of the optical unit (A).

With reference to FIG. 7:

101 is the baseplate (mounting plate)
102 is the holder for the measuring window
103 is the measuring window
104 is the opening for the fiber system
105 is the drip edge
106 is the basic product cell body
107 is the product outlet
108 is the product feed with specific three-dimensional form for the alignment
109 is the shearing gap The sample analysis cell can be sealed off with respect to the optical unit in accordance with all the methods known to those skilled in the art. The considerable shearing of the product in the shearing gap is an important factor both in order to obtain a defined sample state, that is to say by means of this shearing agglomerates of pigment particles, for example, are broken up, and also to achieve self-cleaning of the measuring window, which is continually feed of particles possibly remaining caught on the measuring window by the intense shearing of the sample.

A particular advantage of this self-cleaning of the measuring window is that this is also active during the measurement, so that it is not necessary to switch the reflectance sensor on and off frequently for cleaning purposes. Only if the self-cleaning is not sufficient in the case of specific products, mechanical cleaning of the measuring window can additionally be carried out, for example by a wiper, preferably a Teflon strip, being pushed into the gap.

In order to maintain a defined sample state and therefore to achieve comparable measured data, constant shearing of the sample is necessary. This is preferably implemented by means of continuous monitoring of the inlet pressure, i.e. the pressure at the input point of the liquid pigment preparation to the gap.

Pressure monitoring is necessary in order to guarantee defined shearing at the measuring location. If this is ensured by other measures (for example known pump output, viscosity and gap width), pressure measurement can be dispensed with. In the case of a pressure measurement, a number of variants are suggested, specifically the T configuration, the V configuration, a measurement with a pressure sensor through which flow passes, and a hole in the product cell. The construction of the aforementioned configurations is known to those skilled in the art. The selection criterion is the sufficiently accurate measurement of the relatively low pressures, its sensitivity with respect to pressure fluctuations (for example if the product is delivered by a pulsating pump), and the ability to be flushed easily (no dead spaces) or at least to be cleaned.

In a particularly preferred embodiment of the reflectance sensor according to the invention, the pressure sensor is installed in a measuring chamber of very low volume and is protected by a very thin Teflon film against the penetration of liquid pigment preparations used as the sample. In a preferred embodiment, the feed line is oriented upward, so that even when there is a pressure rise up to 2 bar, no product can get into the measuring chamber. As a result, it is merely necessary to renew the hose when there is a sample change.

In a further particularly preferred embodiment, a pressure sensor is incorporated flush in the planar surface of the inlet volume, behind the flow rectifier.

The setting of the inlet pressure depends, inter alia, on the hiding power and on the viscosity of the liquid pigment preparation used as sample. If the sample used is, for example, a coating which does not cover very well, it is necessary to select a product cell with a larger measuring gap than if a coating which covers better is used. The pressure loss then has to be reset.

In the case of the reflectance sensor according to the invention, the sample analysis cell (Bb) can be removed and can be replaced by solid samples, for example metal sheets, films, plastic surfaces or by a calibration standard. For this purpose, the sample analysis unit preferably further contains a holder for samples which have a solid surface. It is thus possible to carry out both wet and dry measurements with the reflectance sensor according to the invention. As a result, for example a comparison between a solid and a liquid sample of a product, for example of a coating, is possible. The reflectance sensor according to the invention thus permits simple comparison of wet and dry measurements.

Figure 8:
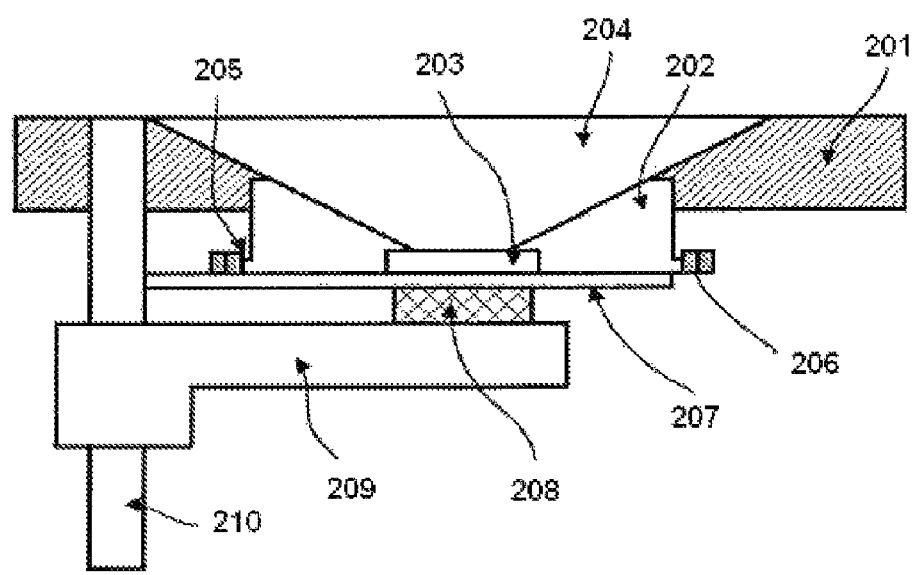
FIG. 8 illustrates an example of a reflectance sensor for measuring solid samples (sheet-metal cell).

FIG. 8 illustrates an example of a reflectance sensor for measuring solid samples (sheet-metal cell).

With reference to FIG. 8:

| | |
|---|---|
| 201 | is the baseplate (mounting plate) |
| 202 | is the holder for the measuring window |
| 203 | is the measuring window |
| 204 | is the opening for the fiber system |
| 205 | is the drip edge |
| 206 | is a spacer |
| 207 | is a solid sample |
| 208 | is a spring element |
| 209 | is a pressure element |
| 210 | is guide rods |

Figure 9:
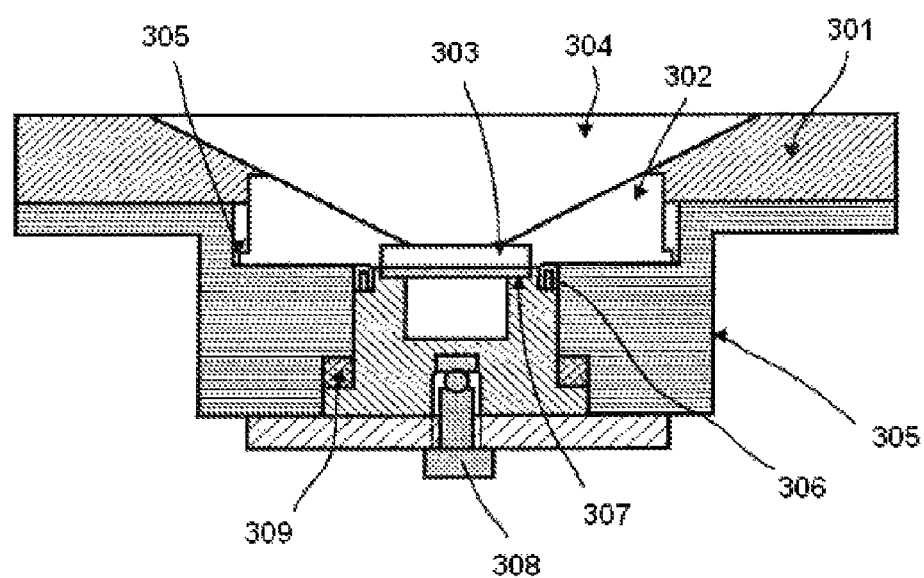
FIG. 9 illustrates an example of a reflectance sensor for measuring a calibration standard (reference cell).

FIG. 9 illustrates an example of a reflectance sensor for measuring a calibration standard (reference cell).

With reference to FIG. 9:

| | |
|---|---|
| 301 | is the baseplate (mounting plate) |
| 302 | is the holder for the measuring window |
| 303 | is the measuring window |
| 304 | is the opening for the fiber system |
| 305 | is the drip edge |
| 306 | is the basic reference cell body |
| 307 | is a spacer |
| 308 | is the reference standard |
| 309 | is a variable pressure system |

A further preferred feature of the reflectance sensor according to the invention is thus the fact that the sample analysis cell (Bb) is removable. In this case, the removal of the sample analysis cell is possible without difficulty and the part of the reflectance sensor which is present following removal of the sample analysis cell is suitable for measuring solid samples (dry measurement) without its being necessary to rebuild the part of the reflectance sensor which is present following removal of the sample analysis cell.

As a holder for samples which have a solid surface (=solid samples), that is to say, for example, for metal sheets, films, plastics or a calibration standard, any holder known to those skilled in the art is suitable. The solid sample is preferably held by guide rods, pressed against the measuring window by a pressure element and sprung by means of a spring element.

c) System Control Unit (C)

The system control unit comprises detectors for recording measured data and an evaluation device connected thereto. The detectors are preferably fiber-optic monolithic diode line spectrometers which permit a resolution of at least 15 bits.

All detectors known to those skilled in the art can be employed; they are preferably fiber-optically coupled monolithic diode line spectrometers, since these are very rugged and stable in terms of the signals. They should have the highest possible resolution, at least 10 bits, preferably from 12 bits, particularly preferably from 15 bits.

In a particularly preferred embodiment of the reflectance sensor, all the units of the reflectance sensor, that is to say the optical unit, the sample analysis unit and the system control unit, are accommodated in a common housing, in which ventilation and thermostat-regulated heat dissipation, particularly preferably by means of cooling water, are carried out (cooler/fan). It is preferably a mobile housing, which can be transported without difficulty to the place of use, for example a housing on rollers. The housing is temperature-controlled, since a constant temperature leads to an improvement in the measuring accuracy. Irrespective of this, it may also be necessary to comply with certain tolerances in the product temperature, since intense evaporation of the solvent, thermal sensitivity and thermochiomatic effects are possible. At the same time, alternating thermal loads, which can lead to mechanical changes, are avoided. Furthermore, the housing prevents the optical waveguides and the other elements of the reflectance sensor being touched and ensures light-tightness. An increase in the measuring accuracy of the reflectance sensor is thus achieved by means of the common housing.

A preferred embodiment of the control unit equalizes the brightnesses of the various optical signals (reference, measurement) by using at least one optical attenuator, in order to be able to drive the spectrometer equally and thus at a maximum. This optimizes the measuring accuracy. These attenuators must keep the set attenuation constant and are preferably continuously adjustable and, particularly preferably, use an electromechanical or piezoelectric precision drive. The attenuators have an input for the fiber optics and an output to the spectrometer. They can be configured from aperture stops, spacers, diffusers, conversion filters and neutral filters; attention must be paid to stability and maintaining complete aperture illumination.

Figure 10A:
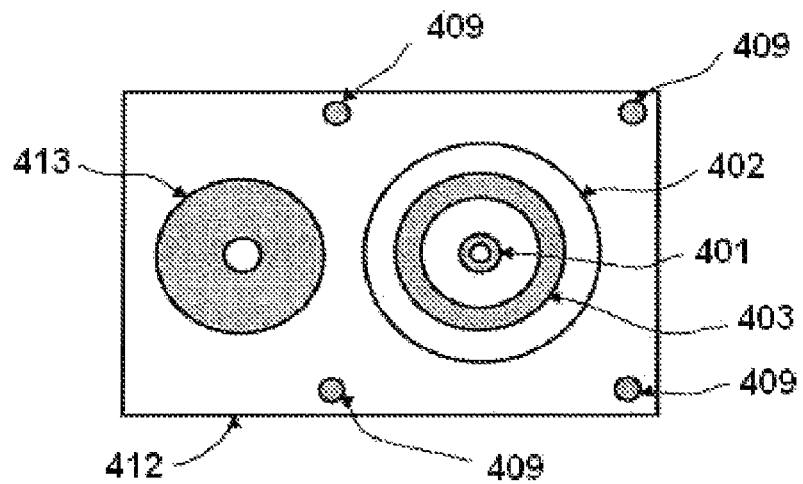
FIG. 10a is a plan view and FIG. 10b is a side view of the attenuator.
Figure 10B:
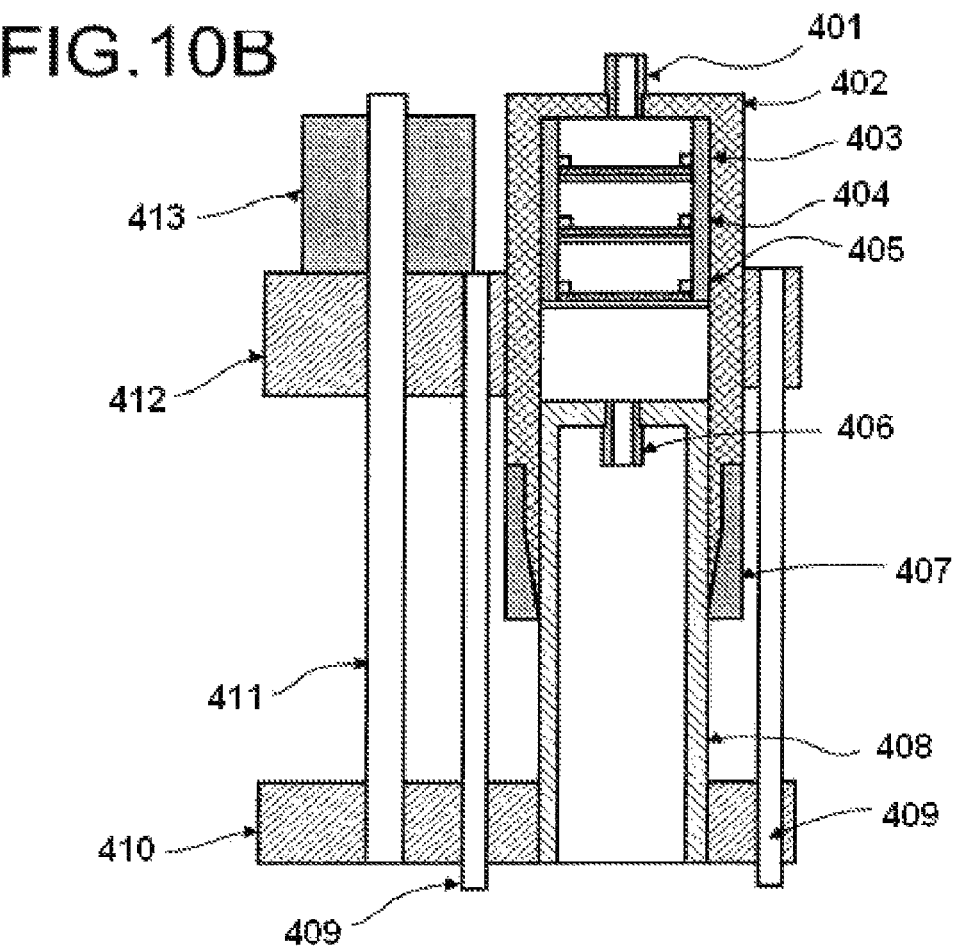

A particularly preferred embodiment of an attenuator is illustrated in FIGS. 10a and 10b. FIG. 10a is a plan view and FIG. 10b is a side view of the attenuator.

With reference to FIGS. 10a and 10b:

| | |
|---|---|
| 401 | is an SMA socket for the receiver |
| 402 | is the basic body |
| 403 | is a diffuser (optional) |
| 404 | is a neutral filter (optional) |
| 405 | is a conversion filter (optional) |
| 406 | is an SMA socket for the transmitter |
| 407 | is a clamping device |
| 408 | is a piston |
| 409 | is guided rods (optional) |
| 410 | is a carriage (optional) |
| 411 | is a drive rod (optional) |
| 412 | is a motor holder (optional) |
| 413 | is a motor |

A system preferably used for reflectance measurement is illustrated in FIG. 11.

Figure 11A:
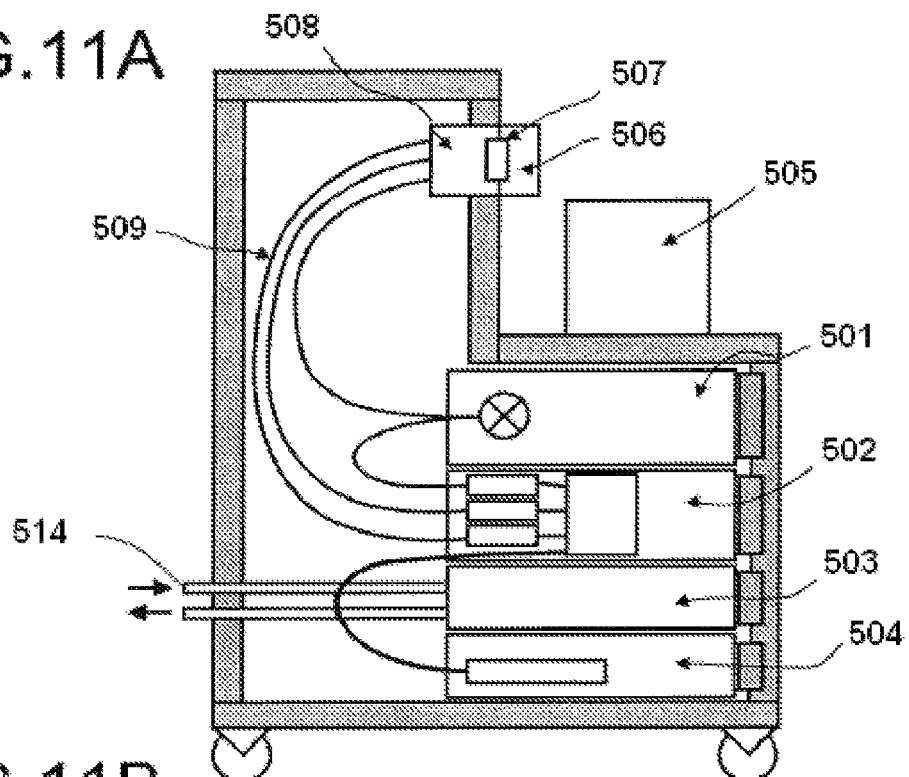
FIG. 11a is a side view and FIG. 11b is a front view.
Figure 11B:
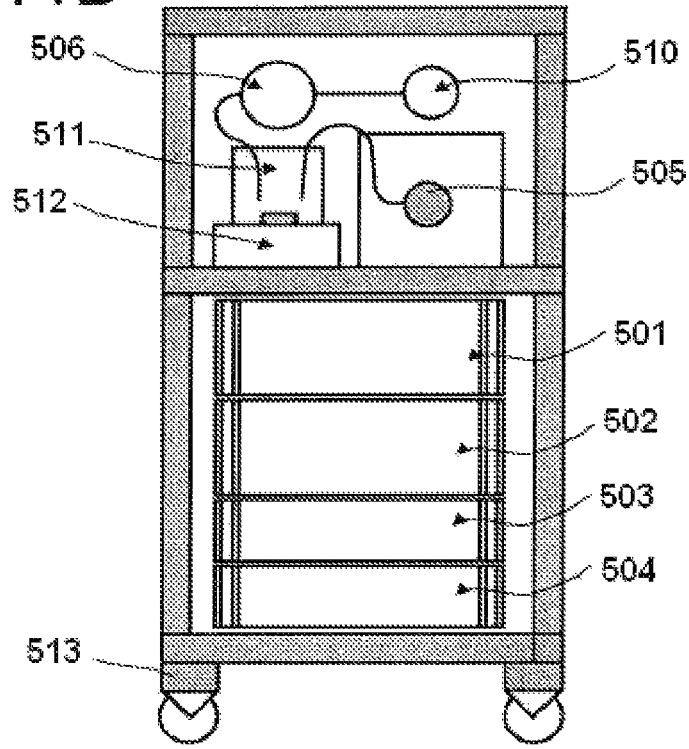

FIG. 11a is a side view and FIG. 11b is a front view.

With reference to FIGS. 11a nd 11b:

| | |
|---|---|
| 501 | is a light source |
| 502 | is a spectrometer with optical attenuator (number: 1-maximum 8) and amplifier |
| 503 | is a cooler |
| 504 | is a PC with AD (analog/digital) converter |
| 505 | is a pump |
| 506 | is the flow cell |
| 507 | is the measuring window |
| 508 | is a fiber holder |
| 509 | is fibers, preferably glass fibers (the number of fibers can be higher than illustrated in the figure) |
| 510 | represents pressure measurement |
| 511 | is a receiving container |
| 512 | is a stirrer, for example magnetic stirrer |
| 513 | is the mobile housing |
| 514 | is cooling water |

Spectrometers 1—maximum 8 (see 2 in FIG. 11) means that each light path to be measured has its own spectral detector (spectrometer).

path 1 normally reference direct from the lamp
path 2 first reflectance angle
path 3 second reflectance angle
path 4 third reflectance angle
path 5 . . .

Figure 12:
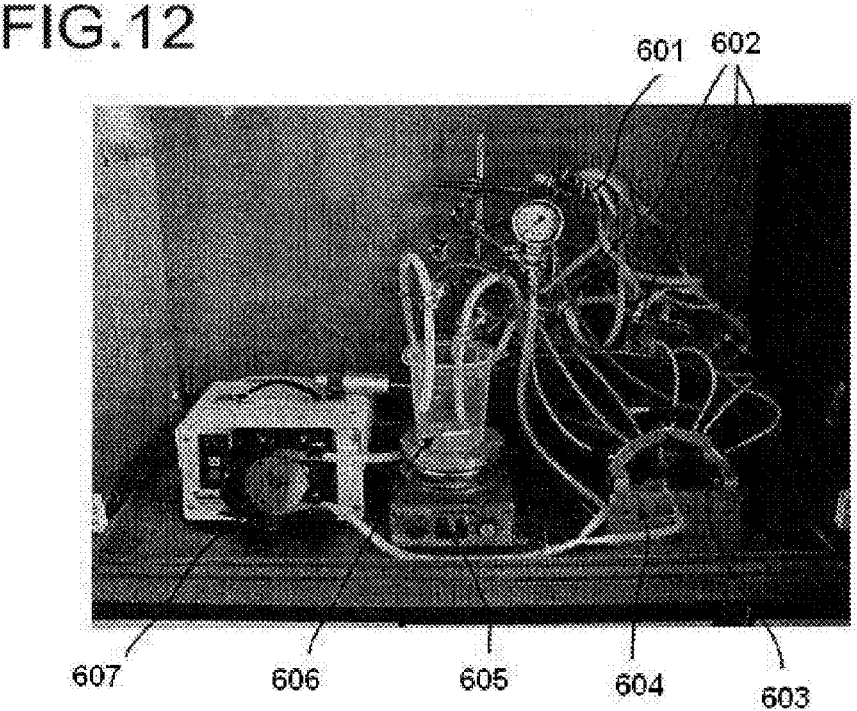
FIG. 12 illustrates a general measurement structure of a highly accurate flow oriented multi angle reflectance sensor (FLOMAC).
Figure 13:
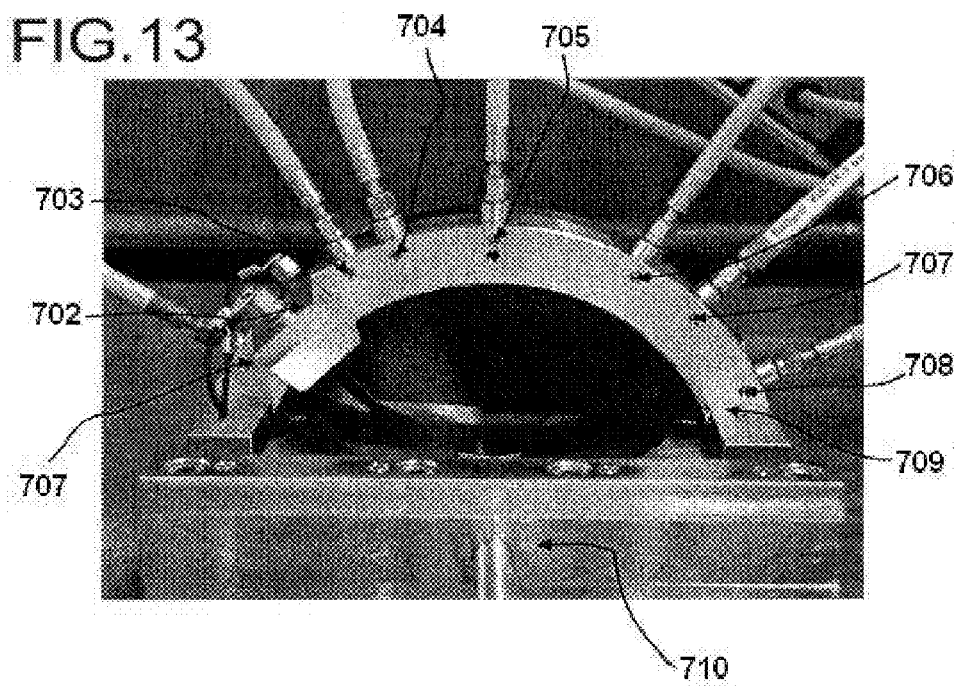
FIG. 13 illustrates optics with illumination at one angle and measurement at a plurality of angles (FLOMAC dome).

The general measurement structure of a highly accurate flow oriented multi angle reflectance sensor is illustrated in FIG. 12, and the optics with illumination at one angle and measurement at a plurality of angles in the form of what is known as a "FLOMAC dome" is illustrated in FIG. 13. FLO-MAC stands for "flow oriented multi angle 5 color sensor".

With reference to FIG. 12:

| | |
|---|---|
| 601 | represents pressure monitoring |
| 602 | is a spectrometer |
| 603 | is the FLOMAC dome |
| 604 | is a FLOMAC cell |
| 605 | is a stirrer |
| 606 | is a receiver |
| 607 | is a pump |

With reference to FIG. 13:

| | |
|---|---|
| 701 | is a receiver at −15° |
| 702 | is a spectrometer |
| 703 | is a receiver at 15° |
| 704 | is a receiver at 25° |
| 705 | is a receiver at 45° |
| 706 | is a receiver at 75° |
| 707 | is illumination |
| 708 | is a receiver at 105° |
| 709 | is the FLOMAC dome |
| 710 | is a FLOMAC cell |

The highest measuring accuracy of the reflectance sensor is achieved if all the aforementioned features are fulfilled in the reflectance sensor. Thus, by using the reflectance sensor according to the invention for measuring liquid samples with non-isometric particles, in particular liquid pigment preparations with non-isometric particles, very high absolute measuring accuracies of, in general, <0.5 to 0.05 dE can be achieved, which is reached by means of an absolute measuring accuracy of 0.1% of the raw measured data (reflectance intensities). In comparison with this, in the case of measurements of solid pigmented surfaces (dry measurements) according to the prior art, absolute measuring accuracies of 0.1 dE are achieved. The reflectance sensor according to the invention is thus suitable to replace complicated dry measurements in the area of measuring samples with non-isometric particles. This is achieved by means of the sensor characteristics of the reflectance sensor according to the invention and by means of the flow cell according to the invention.

Before the start of the measurements, the reflectance sensor must be calibrated. In principle, this can be done in any desired manner known to those skilled in the art. In order to calibrate the reflectance sensor, a white glass plate is preferably used, since this is substantially less susceptible to contamination than a matt surface which is normally used. As compared with the matt surface, the glass has the advantage that it does not age and may be cleaned again and again in a defined manner. The reflective nature of the glass is not critical, since the reflectance sensor masks out the gloss. For the purpose of calibration, the sample analysis cell of the reflectance sensor is taken off.

In a preferred embodiment, the white glass plate (calibration plate) is guided against the measuring window in a precision holder on the guide rods normally carrying the sample analysis unit in a preferred embodiment, and positioned by dowel pins. A spacer ensures a defined and reproducible distance of the white glass plate from the measuring window. Said spacer is advantageously set to values of from 50 to 500 μm, particularly preferably about 100 μm. The glass plate and the spacer are mounted resiliently, preferably via a variable pressure system, for example by means of spring force or an elastomer, so that they always bear flat on the measuring window with a defined pressing force. The reproducibility of this calibration is around 0.1%.

A further advantage of the reflectance sensor according to the invention is that, by using this device, measurements, in particular comparative measurements, can also be carried out with surfaces of corresponding solid samples, for example metal sheets and films, instead of the liquid samples with non-isometric articles, if the sample analysis cell is replaced by the solid samples, for example metal sheets and films. For this purpose, guide rods, in particular the upper guide rods, can be removed. A spacer is generally slipped onto the measuring head (that is to say the measuring window with holder). Placed on the lower rods is a metal sheet, which is pressed against the measuring window by a pressure element guided by these rods. The pressure is applied by a resiliently suspended planar plate of the size of the measuring window. Furthermore, solid and liquid samples without non-isometric particles can also be measured for the purpose of comparison.

The possibility of also measuring solid samples, for example metal sheets, at a defined distance and in a defined alignment with the same optics, is a special feature of the planar design of the measuring window and of the removable product cell. This possibility permits the simple transfer of wet measurements to dry measurements.

A further subject of the present application is a method of measuring the reflectance of a liquid sample containing non-isometric particles, comprising:

i) forming a sample stream of a sample containing non-isometric particles with a defined thickness and defined alignment of the particles in the sample in two axes, ii) irradiating the sample stream at one or more angles with electromagnetic radiation emitted by a light source, the electromagnetic radiation interacting with the sample and some of the radiation being reflected diffusely following interaction with the sample, iii) receiving and registering the diffusely reflected radiation as a reflectance signal at a plurality of angles, iv) receiving and registering a reference signal, the reference signal being electromagnetic radiation which is emitted by the same light source used to irradiate the sample stream but which does not interact with the sample, the reflectance signal and the reference signal being registered simultaneously.

All the signals, that is to say the reflectance signals and the reference signal, are therefore affected by the same random fluctuations. This is achieved by using fiber-optic monolithic diode line spectrometers, which preferably permit a resolution of at least 15 bits and which, with integration times between 4 ms and 6000 ms, are matched to the available brightness. The values measured with such diode line spectrometers relate to a diode number and have to be interpolated to fixed wavelengths. This interpolation is particularly accurate if a spline is used, which is preferred. For this purpose, however, the sensitivity difference between the individual diodes must previously be compensated for, since otherwise overswings occur. This compensation is carried out before the interpolation, by dividing the signals by a pattern which is characteristic of the sensor module.

In order to form the sample stream with a defined thickness and defined alignment of the particles in the sample in two axes, a three-dimensional flow cell according to the present application is preferably used. Preferred embodiments of the flow cell and preferred alignments of the particles have been mentioned above.

In one preferred embodiment, the method according to the invention is carried out with the reflectance sensor according to the invention. Preferred embodiments of the reflectance sensor according to the invention have already been mentioned above.

A further subject of the present application is, therefore, the use of the reflectance sensor according to the invention for measuring the reflectance of a liquid sample containing non-isometric particles.

Figure 14:
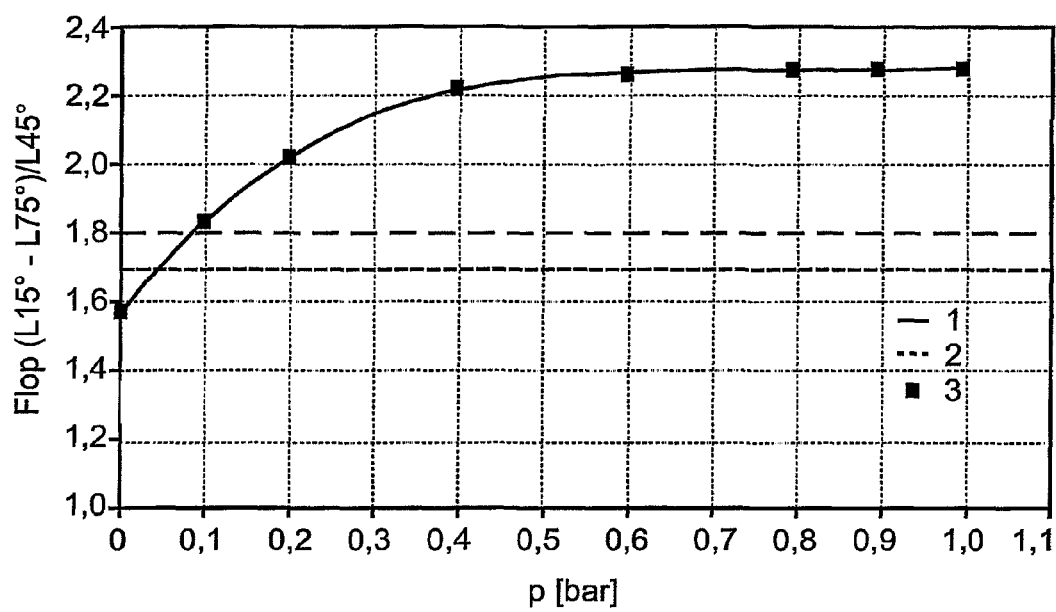
FIG. 14 illustrates measured data which relate to the dependence of the flop on the pressure set in the flow cell and therefore on the flow velocity.

FIG. 14 illustrates measured data which relate to the dependence of the flop ((lightness L at 15° minus lightness L at 75°)/lightness L at 45°) on the pressure set in the flow cell and therefore on the flow velocity. This means that FIG. 14 relates to the flop number of a metallic pigment as a function of the pressure drop in the three-dimensional flow cell according to the invention. Furthermore, for the purpose of comparison, FIG. 14 illustrates individual measurements on metal sheets which are coated with an effect coating containing the metallic pigment (the same coating which is measured as a liquid sample), by means of the reflectance cell according to the invention for measuring solid samples, as described above, and by means of a reflectance sensor according to the prior art (MA 68 II; Multi Angle Spectrophotometer from X-Rite).

With reference to FIG. 14, the x-axis represents pressure, p, in units of bars, and the y-axis represents Flop, which is (L15°−L75°)/L45°. Curve number 1 represents measurements of X-Rite metal sheet (metal sheet measured with a spectrometer from the prior art (MA 68 II; Multi Angle Spectrophotometer from X-Rite)). Curve number 2 represents measurements of dome metal sheet (metal sheet measured with a spectrometer for measuring solid samples according to the present application). Curve number 3 represents measurements of dome liquid (liquid sample, measured with the spectrometer according to the invention for measuring liquid samples).

As can be gathered from FIG. 14, beginning at a specific pressure and thus a specific flow velocity, alignment of the non-isometric metallic pigments in the liquid sample takes place, corresponding to the alignment of the non-isometric metallic pigments on the metal sheets.

Figure 15:
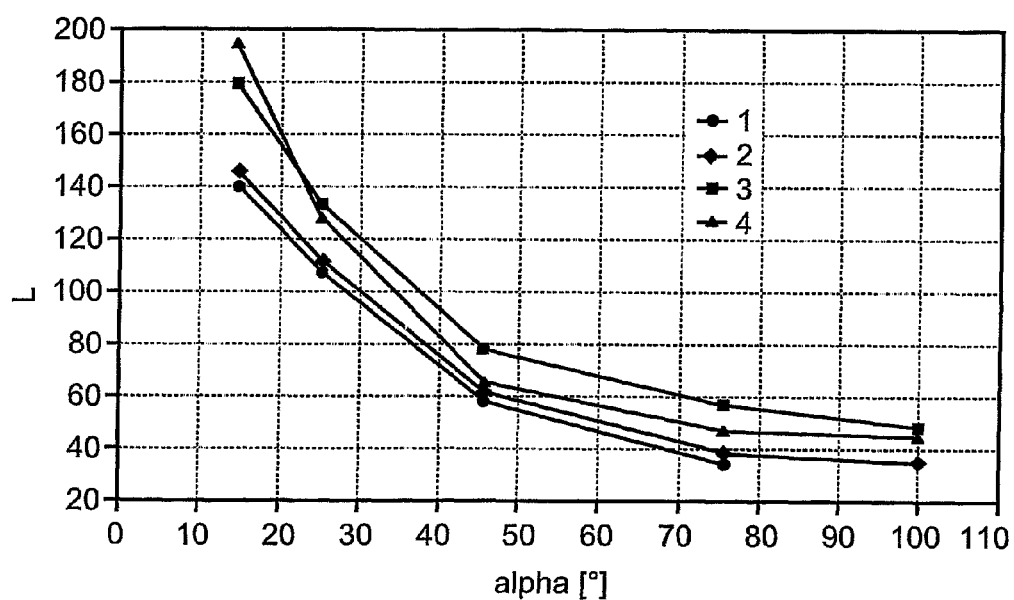
FIG. 15 illustrates measured data which relates to the dependence of the lightness on the reflectance angle relative to the gloss.

In FIG. 15, measured data is illustrated which relates to the dependence of the lightness on the reflectance angle relative to the gloss (angle alpha). In this case, a comparison is illustrated between measured data on coated metal sheets, measured with a reflectance sensor from the prior art (MA 68 II; Multi Angle Spectrophotometer from X-Rite), coated metal sheets measured with the reflectance sensor according to the invention for measuring solid samples, and liquid samples (of the same coating with which the metal sheets have been coated) measured with various embodiments of the reflectance sensor according to the invention for measuring liquid samples, the three-dimensional flow cell being constructed differently in the embodiments.

With reference to FIG. 15, the x-axis represents the reflectance angle relative to the gloss alpha [°], and the y-axis represents Lightness, L. Curve number 1 represents measurements of X Rite metal sheet, curve number 2 represents measurements of dome metal sheet, curve number 3 represents measurements of dome liquid using a symmetrical cell, and curve number 4 represents measurements of dome liquid suing an asymmetrical cell.

All the data is comparable, as can be gathered from FIG. 15. This means that the measurements of the liquid samples supply reliable and comparable data relating to the behavior of non-isometric particles in solid samples.

Figure 16:
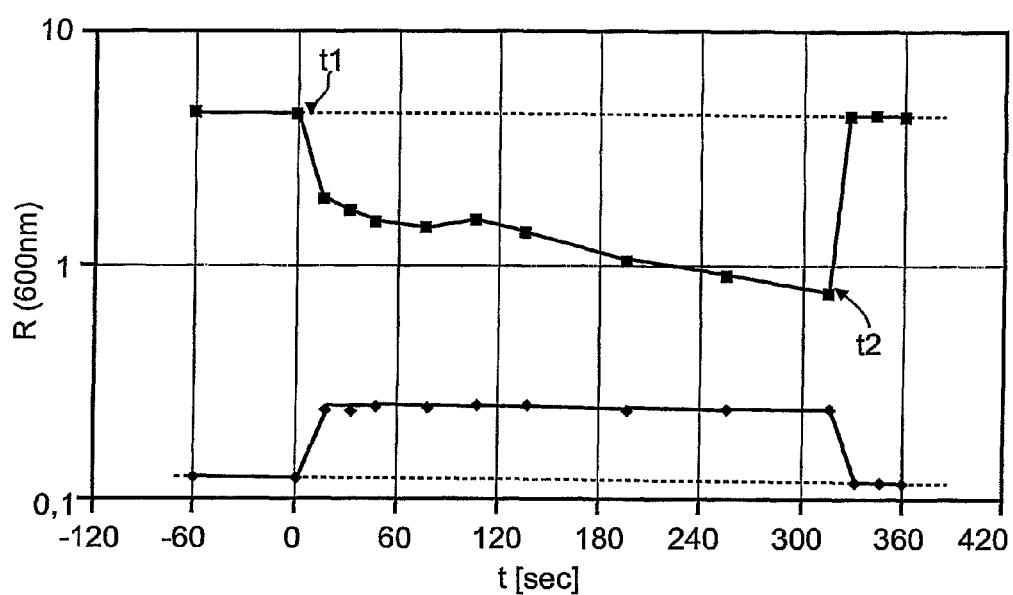
FIG. 16 illustrates measured data from liquid samples containing metallic pigments.

FIG. 16 illustrates measured data from liquid samples containing metallic pigments. In this case, the reflectance is measured as a function of whether there is flow of the liquid sample (pump on) or not (pump off).

With reference to FIG. 16, the y axis represents Reflectance, R, at 600 nm, the observation angles are 15° and 100°, and the pump is off at time "t1" and on at time "t2".

In FIG. 16, the change in the reflectance of the sample when the pump is switched off, that is to say there is no flow of the sample, and therefore no alignment of the non-isometric aluminum effect pigments, can be seen clearly.

The reflectance sensor according to the invention can thus be used, for example, in the following applications:

1. Assessment of pigment properties with test mixtures
   In a similar way to that in which a commercial isometric pigment can be characterized completely in let-downs with white and black, a mixture of metallic or effect pigments with white and black can be used to characterize the flop properties.

2. Control of a metering system
   The advantage—replacement of the time-consuming production of coated sample 10 panels by simple wet measurement—also applies in the production of coatings by means of mixtures of various liquids, for example with a metering system. In this case, it is not the dispersion process but the metering process which is regulated in order to achieve the desired color.

3. Automatically regulated color adjustment during coating production
   The adjustment of a coating to an exact color, "tinting" (=addition of "auxiliary pigments" for color matching) is nowadays carried out by means of manual sampling, possibly application, measurement, addition of pigment dispersions, in a repeated sequence. Automation of the process with the aid of an inline reflectance measurement is not possible because of the inadequate accuracy of the available measuring instruments. A reflectance measuring instrument which can be used inline with high accuracy would open up the possibility of an automatically controlled tinting process.

4. Color matching in a coating installation

The color of the coating may also be matched immediately before coating, by a metering system for color pastes being integrated into the coating installation (see Color-on-Demand, PPG company), and the control of the admixing is carried out via a color measurement of the liquid coating which, in this case, should preferably be carried out inline.

5. Monitoring subsequent color changes

As a result of ageing or shear stressing, pigment pastes or coatings can subsequently change their color. Monitoring the constancy of the color with a highly accurate measuring method—preferably used inline—would be helpful.

6. Monitoring product quality in ring mains of typical ring main installations (for example automobile producers).

A further subject of the present application is thus the use of the reflectance sensor according to the invention for reflectance measurement of liquid pigment preparations containing non-isometric particles at any desired process stage during the production, further processing and use of liquid pigment preparations, preferably for quality control during the dispersion of pigmented coatings and pigment pastes, for quality assessment during coating production, for controlling a metering system during the production of coatings by mixing various liquids, for automatically regulated color adjustment by means of tinting during coating production, for matching the color of the coating in a coating installation which has a metering system for color pastes or for monitoring subsequent color changes as a result of ageing or shear stressing of pigmented coatings or pigment pastes.

A further subject of the present application is the use of the reflectance sensor according to the invention for carrying out the method according to the invention.

It is known that, in the case of effect coatings, that is coatings which contain metallic pigments and/or effect pigments as non-isometric particles, the type of application has a great influence on the appearance of the coating, which to some extent is used specifically (for example, applied "wet or dry" in order to achieve a higher or lower flop; electrostatic or pneumatic application). It is also known that two effect coatings which are the same with specific application parameters can be different with others. According to current supposition (without being bound to any theory), this can be attributed to the fact that some effect pigments react more quickly or more intensely than others to influences which reduce the level of orientation of the particles. The empirical value is that the smaller particles reduce the level of orientation more quickly. This fits in well with the theoretical hypothesis that the Brownian molecular movement rotates small particles more quickly, and that the smaller particles in thin layers can assume slightly greater angles.

With the aid of the reflectance sensor according to the invention, following the level of orientation over time and the measurement of samples which contain the same particles at different levels of orientation are possible. An important property of the reflectance sensor according to the invention is thus the alignment of the effect pigments in a manner "close to the coating". This means that, with the aid of the reflectance sensor according to the invention, a correlation between the alignment of non-isometric particles and their optical properties is possible. At the same time, it is necessary to take into account that the non-isometric particles, in particular metallic pigments and/or effect pigments, are not always present in a completely aligned orientation.

In the experiment, it is confirmed that an alignment effect, as can be calculated, takes place and can be set specifically within certain limits (see FIG. 15). On this basis, it is possible to match the reflectance sensor according to the invention still better to the requirements of practice, for example by no optimal alignment of particles being set—in the sense of complete alignment—but a partial alignment such as takes place, for example, in a specific coating.

The measurement in two alignments, in which one registers the smaller effect pigments at a considerably reduced level of alignment, can be implemented and permits a certain prediction of the influence of application.

The alignment achieved in the flow field depends firstly on the cross-sectional relationships in the three-dimensional flow cell and, secondly, is dissipated gradually again in the parallel part of the cell by the Brownian molecular movement and the flow gradient which builds up, and also the rotational forces resulting from this. This principle of achieving and measuring different alignments of the particles of a sample is implemented by measuring with two different cells, exchanging the inlet and outlet of the flow cell, or measurement at two different flow velocities or, particularly advantageously, at two different points with different levels of alignment at the start of the measuring zone and at the end.

With the aid of the reflectance sensor according to the invention and the method according to the invention, accurate and rapid determination of the reflectance of liquid samples containing non-isometric particles, in particular of liquid pigment preparations, in particular of coatings, pigment pastes and let-downs with white is possible which, as compared with the likewise highly accurate measurement (dE~0.1) on sprayed surfaces, offers a considerable, economically relevant saving in time. This is possible as a result of two-dimensional alignment of the non-isometric particles with the aid of the three-dimensional flow cell according to the invention. For the first time, reproducible measurement of liquid samples containing non-isometric particles is possible. With the aid of the multi angle measuring device according to the invention, it is also possible for measurements to be performed at various illuminating angles with one reflectance sensor.

The possibility of also measuring solid samples, for example metal sheets, at a defined distance and in a defined alignment with the same optics, is a special feature of the planar design of the measuring window and of the removable product cell. This possibility permits simple transfer of wet measurements to dry measurements.

The invention claimed is:

1. A three-dimensional flow cell for aligning non-isometric particles in a liquid sample in two axes, comprising:
   a feed zone (Z1) for the sample containing non-isometric particles to be aligned,
   an expansion zone (Z2), in which each volume element of the liquid sample is expanded in two axes, in contact with the feed zone (Z1),
   a measurement zone (Z3), in which a reflectance measurement of the liquid sample aligned in two axes is carried out, in contact with the expansion zone (Z2), and
   an outlet zone (Z4), from which the liquid sample exits, in contact with the measurement zone (Z3),
   wherein a fluid element of the sample with the dimensions a, b, c is transformed in the expansion zone (Z2) into a fluid element with the dimensions a×n, b/(n×m), c×m, a being the width, b the height and c the length of the fluid element and n and m being constants which depend on the geometry of the flow cell and wherein n is 1.5 to 7.

2. The three-dimensional flow cell as claimed in claim 1, wherein n=m.

3. A method of aligning non-isometric particles in a liquid sample in two axes, comprising the step of passing the liquid sample through a three-dimensional flow cell, wherein a fluid element of the liquid sample with the dimensions a, b, c is transformed into a fluid element with the dimensions a×n, b/(n×m), c×m, a being the width, b the height and c the length of the fluid element and m and n being constants which depend on the geometry of the flow cell and wherein n is 1.5 to 7.

4. The method as claimed in claim 3, wherein n=m.

5. A photometric measuring device for measuring the level of attenuation in the propagation of light in a liquid sample containing non-isometric particles, comprising the three-dimensional flow cell as claimed in claim 1.

6. The photometric measuring device as claimed in claim 5, wherein the photometric measuring device is a reflectance sensor.

7. A reflectance sensor, comprising
a) an optical unit (A), which comprises
aa) a light source (Aa) in the form of a lamp, and
ab) an optical waveguide (Ab) comprising fiber optics, at least one optical waveguide being a reference waveguide;
b) a sample analysis unit (B), which comprises
ba) a measuring window (Ba), and
bb) a sample analysis cell comprising the three-dimensional flow cell of claim 1,
wherein the liquid sample measuring zone (Z3) is defined by a gap between the measuring window (Ba) and the three-dimensional flow cell, and
the optical unit is arranged on the side of the measuring window opposite the measuring zone (Z3); and
c) a system control unit (C) comprising one or more detectors (Ca) for recording measured data and an evaluation device (Cb) connected thereto,
at least one optical waveguide connection being led from the light source (Aa) to the measuring window (Ba) and from the measuring window (Ba) onward to the one or more detectors (Ca), to generate a measured signal, and
at least one reference waveguide connection being led directly from the light source (Aa) to the one or more detectors (Ca) or from the measuring window (Ba) to the one or more detectors (Ca), to generate a reference signal.

8. The reflectance sensor as claimed in claim 7, wherein the lamp is selected from the group consisting of LEDs, gas discharge lamps and lamps with incandescent filaments.

9. The reflectance sensor as claimed in claim 7, wherein the lamp has an integrated shutter.

10. The reflectance sensor as claimed in claim 7, wherein the optical waveguides are fibers of 100 μm, 200 μm, 400 μm, 600 μm or 800 μm fiber diameter.

11. The reflectance sensor as claimed in claim 7, wherein the fiber used as a reference waveguide has a smaller diameter than the remaining optical waveguides.

12. The reflectance sensor as claimed in claim 7, further comprising at least one of the following features:
ac) a compensation filter arranged between the lamp and the measuring window (Ba), which linearises the spectrum of the lamp in such a way that the difference between the highest and lowest intensity of the light emitted by the lamp is a maximum of a factor 4,
ad) an IR blocking filter, a condenser and a diffuser arranged between the lamp and the compensation filter,
ae) optical waveguides inside of protective tubes and supported over their entire length by means of a supporting frame,
af) a reference waveguide having a precise spacing element with incorporated diffuser arranged between the light source (Aa) and the detector (Ca) to maintain the full aperture angle.

13. The reflectance sensor as claimed in claim 7, wherein the measuring window is a planar plate.

14. The reflectance sensor as claimed in claim 7, wherein the gap is 2 to 10 mm long and between 0.05 and 5 mm high.

15. The reflectance sensor as claimed in claim 7, wherein, during the traverse of the liquid sample containing particles, considerable shearing of the sample takes place.

16. The reflectance sensor as claimed in claim 7, wherein the sample analysis cell (Bb) is removable.

17. The reflectance sensor as claimed in claim 7, wherein the system control unit has detectors in the form of fiber-optic monolithic diode line sensors which permit a resolution of at least 15 bits.

18. The reflectance sensor as claimed in claim 7, wherein all the units of the reflectance sensor are accommodated in a common housing, in which ventilation and thermostat-regulated heat dissipation are carried out.

19. A method for measuring the reflectance of a liquid sample containing non-isometric particles, comprising:
i) forming a sample stream of a sample containing non-isometric particles with a defined thickness and defined alignment of the particles in the sample in two axes,
ii) irradiating the sample stream at one or more angles with electromagnetic radiation emitted by a light source, the electromagnetic radiation interacting with the sample and some of the radiation being reflected diffusely following interaction with the sample,
iii) receiving and registering the diffusely reflected radiation as a reflectance signal at a plurality of angles,
iv) receiving and registering a reference signal, the reference signal being electromagnetic radiation which is emitted by the same light source used to irradiate the sample stream but which does not interact with the sample,
wherein the reflectance signal and the reference signal are registered simultaneously.

20. A method according to claim 19 wherein the reflectance is measured by a reflectance sensor comprising
a) an optical unit (A), which comprises
aa) a light source (Aa) in the form of a lamp, and
ab) an optical waveguide (Ab) comprising fiber optics, at least one optical waveguide being a reference waveguide;
b) a sample analysis unit (B), which comprises
ba) a measuring window (Ba), and
bb) a sample analysis cell comprising the three-dimensional flow cell of claim 1,
wherein the liquid sample measuring zone (Z3) is defined by a gap between the measuring window (Ba) and the three-dimensional flow cell, and
the optical unit is arranged on the side of the measuring window opposite the measuring zone (Z3); and
c) a system control unit (C) comprising one or more detectors (Ca) for recording measured data and an evaluation device (Cb) connected thereto,
at least one optical waveguide connection being led from the light source (Aa) to the measuring window (Ba) and from the measuring window (Ba) onward to the one or more detectors (Ca), to generate a measured signal, and at least one reference waveguide connection being led directly from the light source (Aa) to the one or more detectors (Ca) or from the measuring window (Ba) to the one or more detectors (Ca), to generate a reference signal.

21. A method according to claim 19 wherein the reflectance of liquid pigment preparations containing non-isometric particles is determined during at least one of a process stage during production, further processing and use of liquid pigment preparations, quality assessment during coating production, during the production of coatings by mixing various liquids for controlling a metering system, during coating production for automatically regulated color adjustment by means of tinting, in a coating installation which has a metering system for color pastes for matching the color of the coating, monitoring subsequent color changes as a result of ageing or shear stressing of pigmented coatings or pigment pastes or monitoring product quality in ring mains of ring main installations.

22. The method of claim 19, wherein irradiation of the sample is carried out at one or more angles with electromagnetic radiation emitted by a light source and receiving and registering of a reflectance signal is carried out at a plurality of angles.

* * * * *